(12) United States Patent
Enyama et al.

(10) Patent No.: US 8,330,103 B2
(45) Date of Patent: Dec. 11, 2012

(54) CHARGED PARTICLE BEAM APPARATUS AND SPECIMEN INSPECTION METHOD

(75) Inventors: Momoyo Enyama, Kokubunji (JP); Hiroya Ohta, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 766 days.

(21) Appl. No.: 12/213,905

(22) Filed: Jun. 26, 2008

(65) Prior Publication Data

US 2009/0001267 A1    Jan. 1, 2009

(30) Foreign Application Priority Data

Jun. 29, 2007   (JP) ................................. 2007-171750

(51) Int. Cl.
  *G01N 23/00*  (2006.01)
  *G21K 7/00*  (2006.01)
(52) U.S. Cl. ........ 250/310; 250/306; 250/307; 250/311; 250/492.1; 250/492.2; 250/492.3; 250/397; 250/398; 250/396 R
(58) Field of Classification Search .................. 250/306, 250/307, 310, 311, 492.1, 492.2, 492.3, 397, 250/398, 396 R
See application file for complete search history.

(56) References Cited

U.S. PATENT DOCUMENTS

| | | | |
|---|---|---|---|
| 7,049,585 B2 | 5/2006 | Nakasuji et al. | |
| 7,109,483 B2 * | 9/2006 | Nakasuji et al. | ............. 250/310 |
| 7,135,676 B2 | 11/2006 | Nakasuji et al. | |
| 7,236,231 B2 | 6/2007 | Nakamura et al. | |
| 7,241,993 B2 | 7/2007 | Nakasuji et al. | |
| 2005/0263715 A1 | 12/2005 | Nakasuji et al. | |
| 2008/0067376 A1 * | 3/2008 | Tanimoto et al. | ............. 250/310 |

FOREIGN PATENT DOCUMENTS

| | | |
|---|---|---|
| JP | 05-194281 | 8/1993 |
| JP | 05-317708 | 12/1993 |
| JP | 2004-319721 | 11/2004 |
| JP | 2005-126315 | 5/2005 |
| JP | 2005-277128 | 10/2005 |
| JP | 2006-19032 | 1/2006 |
| JP | 2006-221870 | 8/2006 |
| WO | WO 02/037527 A1 | 10/2002 |

OTHER PUBLICATIONS

Office Action issued in Japanese Patent Application No. 2007-171750 on Mar. 13, 2012.

* cited by examiner

*Primary Examiner* — Jack Berman
*Assistant Examiner* — Meenakshi S Sahu
(74) *Attorney, Agent, or Firm* — Antonelli, Terry, Stout & Kraus, LLP.

(57) ABSTRACT

In a multi-charged-particle-beam apparatus, when an electric field and voltage on a surface of a specimen are varied according to characteristics of the specimen, a layout of plural primary beams on the surface of the specimen and a layout of plural secondary beams on each detector vary. Then, calibration is executed to adjust the primary beams on the surface of the specimen to an ideal layout corresponding to the variation of operating conditions including inspecting conditions such as an electric field on the surface and voltage applied to the specimen. The layout of the primary beams on the surface of the specimen is acquired as images displayed on a display of reference marks on the stage. Variance with an ideal state of the reference marks is measured based upon these images and is corrected by the adjustment of a primary electron optics system and others.

17 Claims, 16 Drawing Sheets

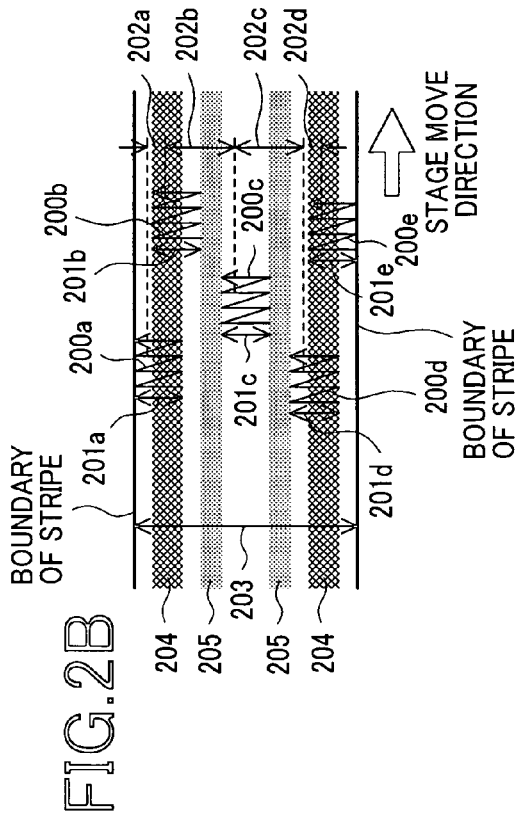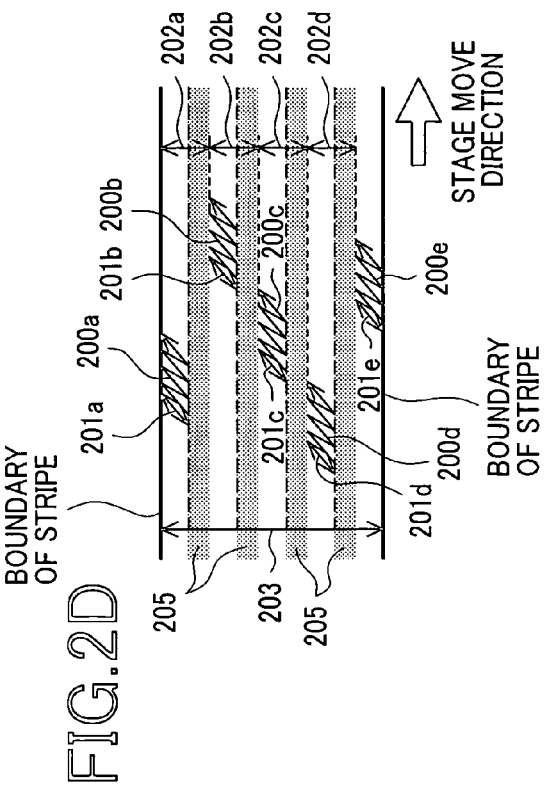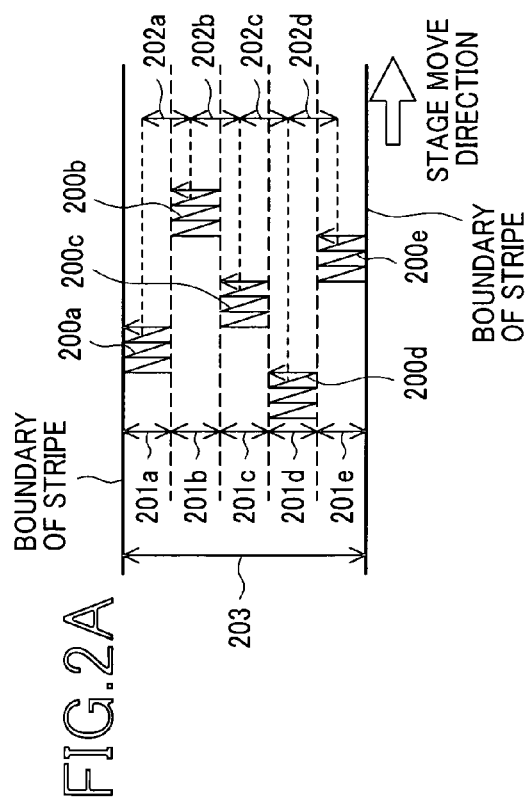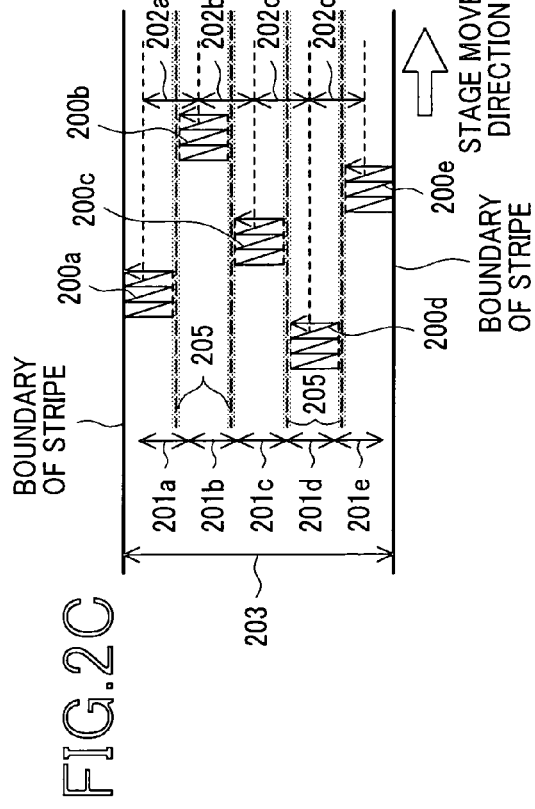

FIG.5

SELECTING INSPECTING CONDITION

500 — FILE NAME [ ▽ ] [REFER]

INSPECTING CONDITION

501 —
| WAFER NAME | **** |
|---|---|
| LANDING ENERGY [keV] | **** |
| PROBE CURRENT [nA] | **** |
| SURFACE ELECTRIC FIELD [V/m] | **** |
| PIXEL SIZE [nm] | **** |
| STAGE MOVE RATE [mm/s] | **** |

[IMPORT] — 503

PARAMETERS

| SETTING INSPECTING CONDITION | | |
|---|---|---|
| FILE NAME | | |

INSPECTING CONDITION

| WAFER NAME | **** |
|---|---|
| LANDING ENERGY [keV] | **** |
| PROBE CURRENT [nA] | **** |
| SURFACE ELECTRIC FIELD [V/m] | **** |
| PIXEL SIZE [nm] | **** |
| STAGE MOVE RATE [mm/s] | **** |

SET — 1600

PARAMETERS

| G1 | ******* | AL1 | ******* | S1 | ******* |
|---|---|---|---|---|---|
| G2 | ******* | AL2 | ******* | S2 | ******* |
| G3 | ******* | AL3 | ******* | S3 | ******* |
| L1 | ******* | AL4 | ******* | S4 | ******* |
| L2 | ******* | ST1 | ******* | S5 | ******* |
| L3 | ******* | ST2 | ******* | S6 | ******* |
| L4 | ******* | ST3 | ******* | S7 | ******* |
| L5 | ******* | ST4 | ******* | S8 | ******* |
| L6 | ******* | V1 | ******* | | |
| L7 | ******* | V2 | ******* | | |
| L8 | ******* | V3 | ******* | | |

500 — FILE NAME
501 — INSPECTING CONDITION table
502 — PARAMETERS table

CHARGED PARTICLE BEAM APPARATUS AND SPECIMEN INSPECTION METHOD

CLAIM OF PRIORITY

The present application claims priority from Japanese patent application JP2007-171750 filed on Jun. 29, 2007, the content of which is hereby incorporated by reference into this application.

BACKGROUND OF THE INVENTION

The present invention relates to a charged particle beam apparatus, particularly relates to technique for executing high-speed and high-precision inspection using multi-beams.

In a process for manufacturing a semiconductor device and a magnetic disk, there are used an electron beam metrology system that emits a charged particle beam (hereinafter called a primary beam) such as an electron beam and an ion beam on a specimen, acquires a signal of a generated secondary charged particle (hereinafter called a secondary beam) such as a secondary electron and measures a contour and dimensions of a pattern formed on the specimen and an electron beam inspection system that probes whether a defect exists or not.

In such a charged particle beam apparatus, the enhancement of speed at which a specimen is processed, that is, inspection speed is an important subject together with the enhancement of defect detection sensitivity. To achieve this subject, a multi-charged-particle-beam apparatus using plural beams is proposed. In such a multi-charged-particle-beam apparatus, the adjustment of beams is important and for example, in WO2002/037527, an electron beam adjustment method of matching a beam layout on a specimen and coordinate axes on a specimen surface by using a rotation lens or rotating a multi-aperture board around an optical axis in a multi-electron-beam inspection system is disclosed.

In the meantime, techniques using multi-beams have been utilized in a field of a mask-less lithography system. When multi-beams are used for a lithography system, a range exposed by each beam is determined and as a writing pattern is required to be precisely grasped, the precise adjustment of an exposure spot and a region scanned by the exposure spot is essential. For example, in JP-A No. 2005-277128, a method of measuring the variance from a defined position of an exposure spot beforehand and correcting each beam is disclosed.

BRIEF SUMMARY OF THE INVENTION

For example, when a contour of a semiconductor wafer is measured, or, defects of a semiconductor wafer are inspected by a charged particle beam at high speed, primary beam raster-scans with a stage continuously moved in one direction. An outline of raster scanning in a multi-electron-beam inspection system that scans a specimen using such plural primary beams and a caused problem will be described below, referring to FIGS. 2A to 2D. In FIGS. 2A to 2D, five beams are used, however, independent of the number of beams, the problem is similar.

FIG. 2A is an explanatory drawing for explaining raster scanning in an ideal layout when primary beams reach a surface of a specimen. Paths on the specimen of five primary beams $200a$, $200b$, $200c$, $200d$, and $200e$ are shown by arrows. Primary beam intervals $202a$, $202b$, $202c$, $202d$ when positions of the five primary beams $200a$ to $200e$ are projected in a direction perpendicular to a stage move direction are equal at arbitrary time. The primary beams $200a$, $200b$, $200c$, $200d$, $200e$ raster-scan the specimen in respective deflection width $201a$, $201b$, $201c$, $201d$, and $201e$. At this time, each deflection width $201a$ to $201e$ is equal and is equal to each beam interval $202a$ to $202d$. The stage is continuously moved in the stage move direction shown by an arrow in FIG. 2A and the beam intervals $202a$ to $202d$ or width of a field-of-view 203 equivalent to five times of each deflection width $201a$ to $201e$ are thoroughly scanned by the five primary beams. Independent of the number of primary beams, the specimen can be thoroughly raster-scanned by plural primary beams.

However, when the layout of the primary beams is variant with the ideal layout on the surface of the specimen, raster scanning shown in FIG. 2A without an unscanned location and overlap becomes impossible. FIGS. 2B to 2D show examples of variance in layouts of primary beams.

FIG. 2B shows a case that the layout of the primary beams is rotated from the ideal layout on the surface of the specimen. Primary beam intervals $202a$ to $202d$ when positions of the five primary beams $200a$ to $200e$ are projected in a direction perpendicular to a stage move direction are not equal differently from those in FIG. 2A. When deflection width $201a$ to $201e$ and a deflection direction (the direction perpendicular to the stage move direction) are the same as those in FIG. 2A, regions 204 each of which the primary beams doubly irradiate and regions 205 each of which no primary beam irradiates are caused. Further, width of a field-of-view 203 is narrower than that in FIG. 2A. When the deflection width $201a$ to $201e$ is made wider than that in FIG. 2A, the region 205 which no primary beam irradiates can be eliminated, however, the regions 204 each of which the primary beams doubly irradiate increase. Conversely, when the deflection width $201a$ to $201e$ is made narrower than that in FIG. 2A, the region 204 which the primary beams doubly irradiate can be eliminated, however, the regions 205 each of which no primary beam irradiates increase.

FIG. 2C shows a case that the layout of the primary beams is wider on the surface of the specimen than those in the ideal layout. When deflection width $201a$ to $201e$ and the deflection direction (a direction perpendicular to a stage move direction) are the same as those in FIG. 2A, width of a field-of-view 203 is wider than that in FIG. 2A, however, regions 205 each of which no primary beam irradiates are caused. When the deflection width $201a$ to $201e$ is wider than that in FIG. 2A, the region 205 which no primary beam irradiates is eliminated and inspection without gap is enabled. However, as the overall magnification of a primary optics system is increased, a beam diameter cannot be stopped down enough. In addition, deflection aberration increases because the deflection width $201a$ to $201e$ is wider. Therefore, desired spatial resolution may not be acquired. Conversely, when the layout of the primary beams is narrower on the surface of the specimen than those in the ideal layout, regions each of which the primary beams doubly irradiate increase though the regions are not shown. When the deflection width is made narrower, inspection without gap is enabled, however, a problem that the width of a field-of-view is made narrower occurs.

FIG. 2D shows a case that a primary-beam deflection direction is variant with a direction perpendicular to a stage move direction. When deflection width $201a$ to $201e$ is the same as that in FIG. 2A, regions 205 each of which no primary beam irradiates are caused. When the deflection width $201a$ to $201e$ is made wider than that in FIG. 2A, the regions 205 each of which no primary beam irradiates are eliminated and inspection without gap is enabled. However, as deflection aberration increases because the deflection width $201a$ to $201e$ is made wider, desired spatial resolution may not be acquired.

An object of the invention is to provide configuration in which high-speed and high-precision calibration is enabled even if a layout of primary beams on a surface of a specimen varies depending upon a condition of inspection and an inspection method using the configuration in a charged particle beam apparatus using multi-beams.

To achieve the object, in a first embodiment of the invention, in a multi-charged-particle-beam apparatus, means for acquiring an image of each reference mark in a layout of primary multi-beams on a surface of a specimen, measuring variance with ideal one and correcting the variance by the adjustment of an electron optics system are provided. In another embodiment of the invention, means for making mechanical parameters which are not electron optical parameters and correcting variance with an ideal state by the adjustment of these are provided.

To avoid an effect of FIGS. 2B to 2D, before inspection is executed, measuring and adjusting the variance of a layout of primary multi-beams on a surface of a specimen with an ideal layout, that is, the calibration of primary multi-beams is required.

Particularly, in an electron beam inspection system, inspecting conditions such as an electric field on a surface of a specimen and voltage applied to the specimen are varied according to characteristics of the specimen. As a layout on the surface of the specimen of primary multi-beams varies depending upon respective inspecting conditions, the above-mentioned calibration is essential.

In the invention, for a specimen inspecting method of illuminating charged particle beams onto a specimen on a movable stage and inspecting the specimen utilizing generated secondary charged particle beams, the calibration of primary multi-beams is executed by forming plural charged particle beams, irradiating the specimen by these plural charged particle beams using a primary optics system, making plural secondary charged particle beams generated from plural locations on the specimen reach signal detectors using a secondary optics system, making the detectors individually detect, processing signals detected by the detected plural secondary charged particle beams, displaying images of the specimen on a display, measuring respective positions on the specimen which the plural charged particle beams irradiate using the displayed images of the specimen, and adjusting the primary optics system based upon the measured respective positions.

Further, the calibration of plural secondary beams is executed by measuring quantity in which the plural secondary charged particle beams irradiate the signal detectors and adjusting positions on the secondary charged particle beam detectors which the plural secondary charged particle beams irradiate based upon the measured results.

Take notice that in this specification, conditions corresponding to various inspecting conditions in an electron beam inspection system may be called operating conditions in the case of a charged particle beam apparatus.

According to the invention, the charged particle beam apparatus and its inspection method in which high defect detection sensitivity and high inspection speed can be made compatible can be realized by executing the calibration of primary multi-beams on the specimen corresponding to the variation of inspecting conditions and others according to characteristics of the specimen in the charged particle beam apparatus using multi-beams and further, executing the calibration of plural secondary beams on secondary charged particle detectors.

BRIEF DESCRIPTION OF THE DRAWINGS

FIGS. 2A to 2D are explanatory drawings for explaining the variance of primary-beam layouts, which is a subject of the invention;

FIG. 5 shows an inspecting condition selecting window when the calibration of primary beams is executed in the first embodiment;

FIG. 16 shows an inspecting condition setting window in the first embodiment.

DETAILED DESCRIPTION OF THE INVENTION

Figure 1:
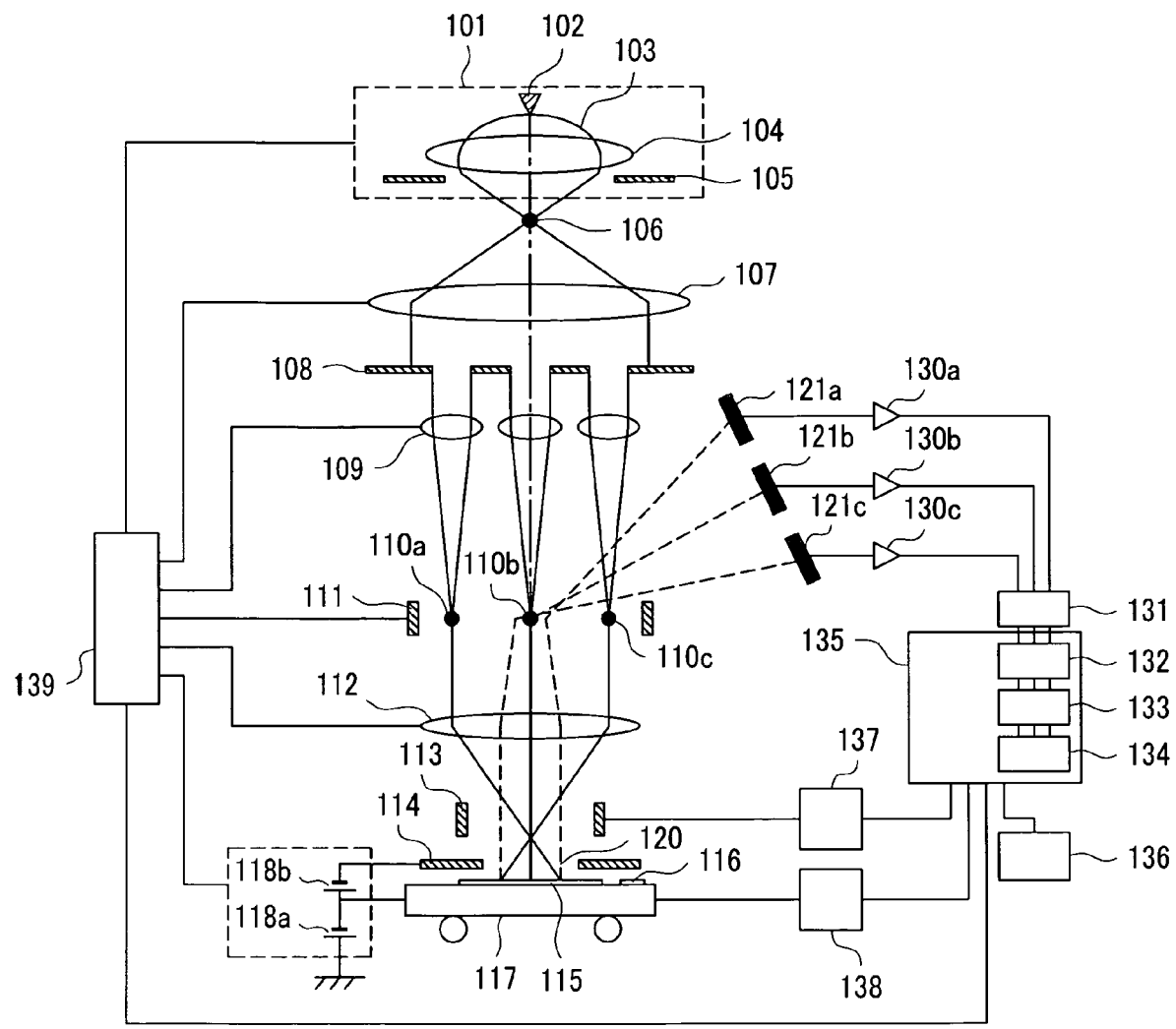
FIG. 1 illustrates the configuration of a multi-electron-beam inspection system equivalent to a first embodiment.

Referring to the drawings, embodiments will be described in detail below. In all the drawings for explaining the embodiments, the same reference numeral is allocated to the same component and its repeated description is omitted. The embodiments related to the electron beam inspection of a semiconductor pattern will be described below, however, when an ion beam is used or when a magnetic disk is inspected, these embodiments can be also applied and the effect is similar. These embodiments can be applied to another charged particle beam apparatus such as a metrology system.

First Embodiment

FIG. 1 shows the schematic configuration of a multi-electron-beam inspection system equivalent to a first embodiment.

First, the configuration of the system will be described. An electron gun 101 includes a cathode 102 made of a material the work function of which is low, an anode 105 having higher electric potential than the cathode 102 and an electromagnetic lens 104 that superposes a magnetic field upon an accelerating electric field formed between the cathode and the anode. In this embodiment, a Schottky cathode in which emission current is large and the emission of an electron is stable is used. In a downstream direction in which a primary electron beam 103 is extracted from the electron gun 101, as shown in FIG. 1, there are arranged a collimator lens 107, an aperture array 108 plural apertures of which are arranged on the same substance, a lens array 109 having plural apertures, a beam separator 111, an objective lens 112, a deflector for scanning 113, a stage 117 and secondary electron detectors 121a to 121c. Further, a condenser aperture, an aligner for adjusting a central axis (an optical axis) of primary beams, an aberration corrector, which are not shown and others are also added to the electron optics system. A wafer 115 is set on the stage 117.

Negative electric potential (hereinafter called retarding electric potential) is applied to the wafer 115 as described later. A wafer holder exists between the wafer 115 and the stage 117 with electricity conducted to the wafer though the wafer holder is not shown and a power supply for retarding voltage 118a is connected to the wafer holder so as to apply desired voltage to the wafer holder and the wafer 115.

A surface-electric-field controlling electrode 114 is installed on the side in a direction of the electron gun of the wafer 115. A scanning signal generator 137 is connected to the deflector for scanning 113 and a power supply for surface-electric-field controlling voltage 118b is connected to the surface-electric-field controlling electrode 114. An electron optics system controller 139 is connected to the electron gun 101, the collimator lens 107, the lens array 109, the beam separator 111, the objective lens 112, the power supply for retarding voltage 118a and the power supply for surface-electric-field controlling voltage 118b, and further, a system controller 135 is connected to the electron optics system controller 139. A stage controller 138 is connected to the stage 117, and further, the secondary electron detectors 121a to 121c and the deflector for scanning 113 are similarly connected to the system controller 135. In the system controller 135, a memory 132, a computer 133 and a defect detecting unit are arranged and a display 136 is connected to the system controller. The components except the control system and the circuit system are arranged in a vacuum housing though the vacuum housing is not shown and it need scarcely be said that the components are operated in a state in which the housing is evacuated. Also needless to say, a wafer carrying system for loading a wafer onto the stage from the outside of the vacuum housing is provided. A reference mark 116 used for adjusting an electron optics condition and measuring an adjusted state is provided onto the stage.

Next, wafer pattern inspection using the electron beam inspection system will be described.

The primary beam 103 emitted from the cathode 102 is accelerated in a direction of the anode 105 while the effect of convergence by the electromagnetic lens 104 is applied and a first electron source image 106 (a point at which a beam diameter is minimum) is formed. An aperture is arranged in the electron gun 101 as a general electron gun is often provided with it though the aperture is not shown so as to pass an electron beam in a range of desired current. The quantity of current in the primary beam that passes the aperture can be adjusted to desired quantity by varying current and voltage applied to the anode 105 and the electromagnetic lens 104. The aligner that corrects the optical axis of the primary electron beam is arranged between the electron gun 101 and the collimator lens 107 is arranged though the aligner is not shown and thereby, the displacement from the aperture and the electron optics system of the central axis of the electron beam can be corrected. The collimator lens 107 substantially collimates the primary beam using the first electron source image 106 as a source. In this embodiment, the collimator lens 107 is an electromagnetic lens. In this embodiment, the aperture array 108 is provided with five apertures and the primary beam is split in fives. In FIG. 1, three beams of these are shown. The split primary beams are individually converged by the lens array 109 to be plural second electron source images 110a, 110b, 110c. The lens array 109 is respectively formed by three electrodes having plural apertures and acts upon each primary beam that passes the aperture as an einzel lens by applying voltage to the central electrode.

The primary beams 103 individually converged by the lens array 109 passes the beam separator 111. The beam separator 111 is used for separating the primary beams 103 and secondary beams 120 and in this embodiment, a Wien filter that generates a magnetic field and an electric field mutually perpendicular in a plane substantially perpendicular to a direction in which the primary beams is incident and applies a deflection angle corresponding to the energy of passing electrons to the passing electrons is adopted. In this embodiment, the strength of the magnetic field and the electric field is set so that the primary beams directly advances and further, the strength of the electromagnetic field is adjusted and controlled so that secondary electron beams incident from a reverse direction is deflected at a desired angle. As for a position of the beam separator 111, in consideration of an effect upon the primary beams of aberration, the beam separator is arranged with the position fitted to the height of secondary electron source images 110a, 110b, and 110c of the primary beams so as to reduce the effect. The objective lens 113 is an electromagnetic lens, reduces and projects the secondary electron source images 110a, 110b, and 110c.

The deflector for scanning 113 is configured in an electrostatic eight-pole type inside the objective lens. When a signal is input to the deflector 113 by the scanning signal generator 137, five primary beams that pass inside the deflector are deflected by the substantially same angle in the substantially same direction and raster-scan the wafer 115 as a specimen. At this time, the ideal layout on the wafer 115 of the primary beams 103 is shown in FIG. 2A.

Negative electric potential is applied to the wafer 115 by the power supply for retarding voltage 118a and an electric field that decelerates the primary beams is generated. The power supply for retarding voltage 118a and the power supply for surface-electric-field controlling voltage 118b are integrally controlled by the system controller 135 via the electron optics system controller 139 like the other optical components, that is, the electron gun 101, the collimator lens 107, the lens array 109, the beam separator 111 and the objective lens 112. The stage 117 is controlled by the stage controller 138. The scanning signal generator 137 and the stage controller 138 are integrally controlled by the system controller 135 so as to inspect a predetermined region on the wafer 115 one by one stripe arranged in a stage move direction and calibration is executed beforehand. The details of the calibration will be described later. In the inspection system equivalent to this embodiment, the stage is continuously moved when inspection is executed and is controlled so that the primary beam sequentially scans a stripe region by the combination of deflection by scanning and the movement of the stage. The stripe region is acquired by dividing the predetermined inspection region and the whole predetermined inspection region is scanned by scanning plural stripe regions.

The five primary beams that reach the surface of the wafer 115 mutually act upon material in the vicinity of the surface of the specimen. Hereby, electrons such as a backscattered electron, a secondary electron and an Auger electron are generated from the specimen to be secondary beams.

The surface-electric-field controlling electrode 114 is an electrode for adjusting field intensity in the vicinity of the surface of the wafer 115 and controlling a path of the secondary beams 120. The surface-electric-field controlling electrode 114 is installed directly above to the wafer 115 and positive electric potential, negative electric potential or the same electric potential to the wafer 115 is applied to the surface-electric-field controlling electrode 114 by the power supply for surface-electric-field controlling voltage 118b.

Voltage applied to the surface-electric-field controlling electrode 114 by the power supply for surface-electric-field controlling voltage 118b is adjusted to an appropriate value according to a type of the wafer 115 and an observed object. For example, when the generated secondary beam 120 is to be positively returned to the surface of the wafer 115, negative voltage is set to the power supply for surface-electric-field controlling voltage 118b. Conversely, positive voltage can be also set to the power supply for surface-electric-field controlling voltage 118b to prevent the secondary beam 120 from being returned to the surface of the wafer 115.

After passing the surface-electric-field controlling electrode 114, the converging action of the objective lens 112 is applied to the secondary beams 120, further, the secondary beams are separated from the path of the primary beams by the beam separator 111 having deflective action, and reach the detectors 121a, 121b, 121c. The detected signals are amplified by amplifiers 130a, 130b, 130c, are digitized by an A/D converter 131, and are once stored in the memory 132 in the system controller 135 as image data. Afterward, the computer 133 computes various statistics from images and finally determines whether defects are included or not based upon a defect determination condition acquired beforehand by the defect determining unit 134. A result of the determination is displayed on the display 136. Regions to be inspected in the wafer 115 can be sequentially inspected from an end according to the above-mentioned procedure.

Next, the details of the calibration of the primary multi-beams in this embodiment will be described.

Before the execution of the calibration of the primary beams, the layout on the wafer 115 of the primary beams 103 may be variant with that in FIG. 2A which is an ideal layout and may be any layout shown in FIGS. 2B to 2D or the combination of them. It is an object of the calibration of the primary multi-beams to measure the quantity of variance and to settle the variance in tolerance.

When the calibration is executed, the stage 117 is moved so that the reference mark 116 exists in a field of view. When the inspection is executed, the stripe region is scanned by the combination of deflection in one direction and the move of the stage, however, while the calibration is executed, the stage 117 is not moved, and a still image is acquired with a deflection direction in two directions of a deflection direction under inspection and its perpendicular direction.

Figure 3A:
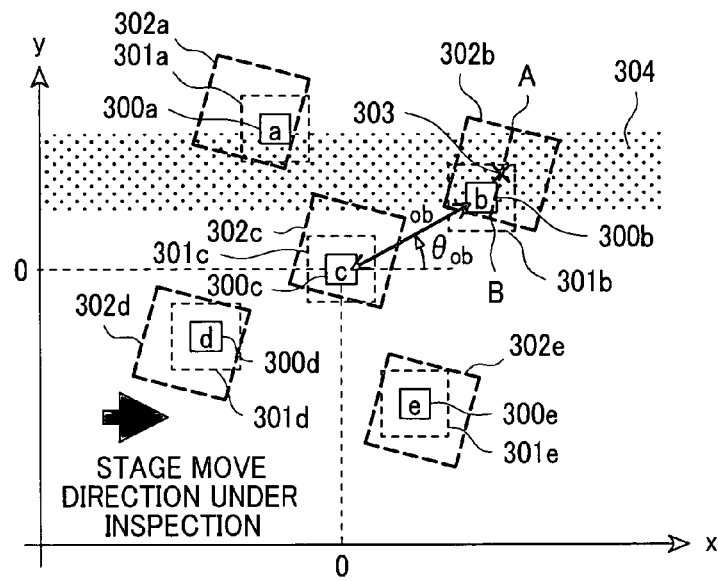
FIGS. 3A to 3C are explanatory drawings for explaining a method of calibrating primary beams equivalent to the first embodiment.
Figure 3B:
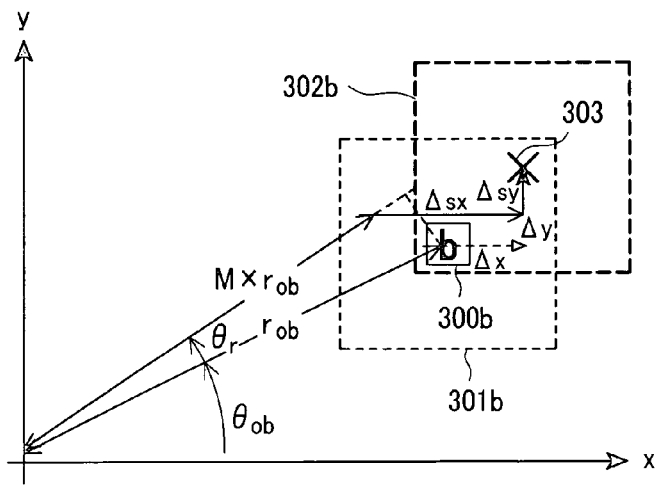
Figure 3C:
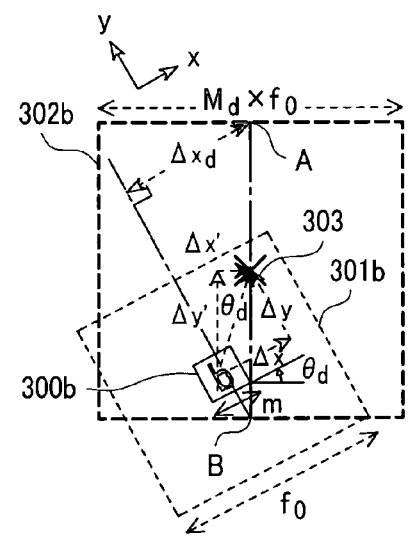

FIG. 3A is a plan showing the vicinity of the reference mark 116 of the stage 117. A stage move direction when the inspection is executed shall be a direction of the x-axis, its perpendicular direction shall be a direction of the y-axis, and a position corresponding to the central axis (the optical axis) of the primary beams shall be an origin. The layout of reference marks 300a to 330e corresponds to that of primary beams 200a to 200e in FIGS. 2A to 2D. In FIGS. 3A to 3C, suppose that images are acquired in scan ranges 302a to 302e for example for ideal scan ranges 301a to 301e. In these acquired images, each reference mark is displaced from the center of each image, these acquired images are rotated, and they are observed in size different from ideal size. For the cause, five items of (1) the rotation of a primary-beam layout, (2) scaling up or down of the primary-beam layout, (3) a shift of the whole primary-beam layout, (4) the variance of deflection width and (5) the variance of a deflection direction respectively to be adjusted by the calibration can be given.

The beam (the primary beam 200b) related to the reference mark 300b as a representative of the five primary beams will be described below. During calibration, the stage 117 is fixed, however, when the inspection is executed, the stage is moved in the direction of the x-axis and a range shown by an alternate long and short dash line of a straight line AB in a scan range 302b is scanned. Therefore, for a range scanned by the primary beam 200b, a region 304 included in a range in which A and B are projected on the y-axis is scanned. Therefore, the completion of calibration is judged by calculating Y-coordinates of A and B per each beam and verifying that distance between them is in predetermined tolerance. However, as shown in FIG. 2D, as the Y-coordinates of A and B may be in the tolerance even if the deflection direction is variant with ideal one, a condition is separately determined as to deflection.

When distance from the origin of the reference mark 300b is r0b and an angle with the x-axis is θ0b, coordinates of the reference mark 300b, that is, central coordinates of an ideal scan range 301b are (r0b cos (θ0b), r0b sin (θ0b)).

Central coordinates 303 of the scan range 302b are displaced from the coordinates of the reference mark 300b because of (1) to (3) of the above-mentioned (1) to (5). FIG. 3B shows the situation. When the whole layout is rotated by θr from ideal one, an angle with the x-axis of the center of the scan range 302b is θ0b+θr. When the magnification of the optics system is different from ideal one, an acquired image is also variant with ideal one as a result. When the magnification of the optics system is magnified M times or is reduced, compared with ideal one, the whole layout is equivalent to M times of ideal one and distance from the origin to the center of the scan range 302b is equivalent to M×r0b. In FIG. 3B, as M is below 1 and it is assumed that the layout is reduced, compared with ideal one, distance from the origin to the center of the scan range 302b is shorter than ideal one. Further, the shifted quantity of the layouts of the whole beams is required to be considered. Suppose that the layouts of the whole beams are shifted by (Δsx, Δsy) from ideal ones. When the above-mentioned variances are all considered, the central coordinates of the scan range 302b change to (M×r0b cos (θ0b+θr)+Δsx, M×r0b sin (θ0b+θr)+Δsy). Therefore, the variance of the layout because of (1) to (3) is as follow.

[Mathematical Expression 1]

$$\Delta x = M \times r0b \cos(\theta 0b + \theta r) + \Delta sx - r0b \cos(\theta 0b) \quad [1]$$

[Mathematical Expression 2]

$$\Delta y = M \times r0b \sin(\theta 0b + \theta r) + \Delta sy - r0b \sin(\theta 0b) \quad [2]$$

In the meantime, the appearance of the acquired image changes because of (4) and (5). FIG. 3C shows the situation. When deflection width is equivalent to Md times of ideal one f0, a size of the reference mark 300b is m for deflection width Md×f0 in the acquired image and its ratio is m/(Md×f0). As the ratio is m/f0 in ideal one, it is observed that the observed size is equivalent to 1/Md of the actual size. Similarly, it is observed that Δx and Δy are also equivalent to 1/Md of the actual sizes. When variance in an angle with the deflection direction is θd, the reference mark is observed in a state in which it is rotated by θd. Therefore, the apparent variance of the layout observed in the acquired image is as follow.

[Mathematical Expression 3]

$$\Delta x' = \sqrt{(\Delta x^2 + \Delta y^2)} \sin(\theta d)/Md \quad [3]$$

[Mathematical Expression 4]

$$\Delta y' = \sqrt{(\Delta x^2 + \Delta y^2)} \cos(\theta d)/Md \quad [4]$$

Difference in size made by the variation of deflection width between the ideal scan range 301b and the scan range 302b is ΔS=(Md−1)f0 and difference by the variation of the deflection direction in X-coordinates at the points A and B is $\Delta xd = M \times f0 \times \sin(\theta d)$. Therefore, a condition for the completion of calibration related to deflection is that $\Delta S$ and $\Delta xd$ are in the tolerance.

In the expressions [1], [2], [3] and [4], $\theta r$, M, $\Delta sx$, $\Delta sy$, Md and $\theta d$ are common parameters to all the primary beams (five in this embodiment). Therefore, the magnification Md of deflection width and a variant angle $\theta d$ with the deflection direction are respectively measured based upon five images in this embodiment acquired by all the primary beams, namely, multi-beams, the above-mentioned apparent variance ($\Delta x'$, $\Delta y'$) of the layout is respectively calculated for all the primary beams (five in this embodiment), $\theta r$, M, $\Delta sx$ and $\Delta sy$ respectively described above can be acquired based upon the expressions [1], [2], [3], [4] in parallel for all the beams, namely, multi-beams, and simultaneously, Y-coordinates of A and B can be acquired.

Optical conditions are varied by feeding back $\theta r$, M, $\Delta sx$ and $\Delta sy$ to the scanning signal generator 137 and the electron optics system controller 139 in parallel for all the beams as multi-beams, the feedback is repeated until the Y-coordinates of A and B, $\Delta S$ and $\Delta xd$ are in the tolerance simultaneously for all the primary beams as multi-beams, and the calibration is completed. In this embodiment, a case that a variant angle $\theta d$ with the deflection direction and the magnification Md of deflection width are the same in the direction of the x-axis and in the direction of the y-axis is supposed, however, in a case that they are different in the direction of the x-axis and in the direction of the y-axis, calibration is similarly enabled by increasing parameters.

Further, when the tolerance is made wider, it is allowed by varying deflection width that a region which electron beams doubly irradiate is caused and scanning without gap is enabled or conversely, such scanning that a region which no electron beam irradiates is caused is enabled.

The tolerance of calibration can be arbitrarily set, however, its concrete example will be described below. For the convenience of explanation, the number of multi-beams is set to n, deflection width 201 per one beam is set to S, and width of a field-of-view 203 acquired by n pieces of beams is set to F (see FIGS. 2A to 2D).

When it is allowed that a region which beams doubly irradiate is caused, it is desirable that the width of a field-of-view F meets a conditional expression, $(n-1)S \leq F \leq nS$. That is, it is allowed that the width of a field-of-view equivalent to the deflection width of one beam is sacrificed, a region which beams doubly irradiate is formed, and the width of a field-of-view which cannot be acquired by (n−1) pieces of beams can be realized. Hereby, the wider width of a field-of-view which cannot be acquired by (n−1) pieces of beams can be realized and a scanned image (an SEM image) can be efficiently acquired, compared with (n−1) pieces of beams. When it can be allowed that a region which no electron beam irradiates is formed, it is desirable that a conditional expression, $nS < F \leq (n+1)S$ is met. That is, the width of a field-of-view equivalent to the deflection width of one beam is allowed as a region which no electron beam irradiates and the width of a field-of-view wider than nS can be realized. Hereby, a scanned image can be efficiently acquired, compared with a case that it is not allowable that there is a region which is not irradiated by n pieces of electron beams and throughput per unit area can be enhanced. The reason why (n+1)S is set to an upper limit is that a region which no electron beam irradiates is too large when this value is exceeded and the omission of acquiring a scanned image may have a bad effect. Further, in consideration of these two elements, such calibration that $(n-1)S \leq F \leq (n+1)S$ is met is executed and beams, namely, multi-beams can be also scanned. Hereby, at least $F < (n-1)S$ or $(n+1)S < F$ does not come into effect and a bad effect by the too narrow or too wide width of a field-of-view can be inhibited. Repetitive operation in calibration can be reduced by increasing the tolerance of F, compared with a case in consideration of one element and time related to calibration can be reduced.

Next, a concrete example of tolerance when n pieces of beams are divided into two groups and scanning by the beams is made will be described. In this case, for the convenience of explanation, the beams are divided into a group A and a group B. For a case that the beams are divided into two groups, a case that the group A is used for a scanning beam for pre-charge for electrifying the surface of the specimen and the group B is used for a scanning beam for acquiring a secondary electron image of a precharged region or a case that secondary electron images of the same region are acquired using the groups A and B for a scanning beam for acquiring a secondary electron image and the mutual secondary electron images are compared is conceivable. In this case, when "n" is even, the beams are classified into the group A and the group B every n/2 and when "n" is odd, the beams are classified into (n−1)/2 and (n+1)/2. To explain n/2 as "k" when n is even and (n−1)/2 as "k" when n is odd, it is desirable for the similar reason to the above-mentioned that the width of a field-of-view meets any conditional expression of $(k-1)S \leq F < kS$, $kS < F \leq (k+1)S$ and $(k-1)S \leq F \leq (k+1)S$. The reason why (n−1)/2 is k when n is odd is that the number of beams is set to a small number.

Next, a concrete example of tolerance when a region which no electron beam irradiates is made wide between beams will be described. This reason is that there is a case that it is difficult to detect with secondary beams split because primary beams are close and there is a case that a beam interval dares to be made wide. A case that an interval between beams is secured by one deflection width will be described below. In this case, as the width of a field-of-view per one beam can be regarded as 2S, it is desirable that the width of a field-of-view meets any conditional expression of $(k'-1)S \leq F < k'S$, $k'S < F \leq (k'+1)S$ and $(k'-1)S \leq F \leq (k'+1)S$ for the similar reason to the above-mentioned to explain 2 n as k'. As for a region which no electron beam irradiates between beams, beam scanning is also enabled in the region between beams by substituting the region which no electron beam irradiates for a region once scanned and separately executing multi-beam scanning. This can be easily realized by displacing the stage by one deflection width for example.

Next, a concrete example of tolerance when n pieces of beams in this case are divided into two groups will be described. In this case, when "n" is even, the beams are also classified into a group A and a group B every n/2 and when "n" is odd, the beams are classified into (n−1)/2 and (n+1)/2. To explain n/2 as k" when n is even and (n−1)/2 as k" when n is odd, it is desirable for the similar reason to the above-mentioned that the width of a field-of-view meets any conditional expression of $(k''-1)S \leq F < k''S$, $k''S < F \leq (k''+1)S$ and $(k''-1)S \leq F \leq (k''+1)S$. The reason why (n−1)/2 is k" when n is odd is that the number of beams is set to a small number.

The examples of the tolerance of the calibration have been described. As described above, various conditions are met and in addition, the specimen can be scanned by plural charged particle beams respectively by calibrating the width of a field-of-view using the conditions of the number of beams and beam deflection width, and the above-mentioned various effects can be acquired.

Next, referring to FIGS. 15, 16, 4, 5 and 6, a procedure for the above-mentioned calibration will be described.

Calibration is executed after inspecting conditions are set. As an inspecting condition, that is, an operating condition is varied according to a characteristic of the specimen in the electron beam inspection system and inspection is required to be executed, each inspecting condition is stored in the memory 132. As a layout of primary multi-beams on the surface of the specimen varies depending upon an inspecting condition, the above-mentioned calibration is required to be executed every inspecting condition. Then, in this embodiment, the inspecting condition stored in the memory 132 is read, calibration is executed every inspecting condition, and a result of the calibration is stored in the memory 132.

Figure 15:
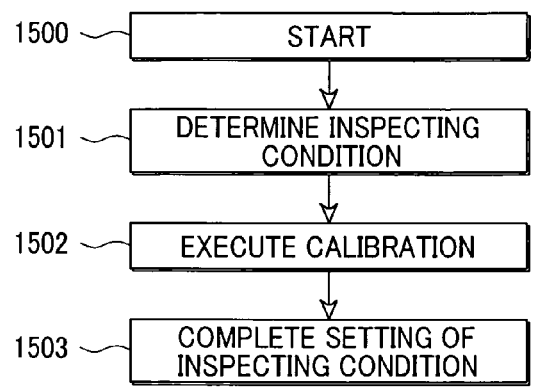
FIG. 15 is a flowchart showing a procedure for setting inspecting conditions in the first embodiment.

FIG. 15 is a flowchart showing a procedure for setting an inspecting condition. When an operator clicks an inspecting condition setting button displayed on the display 136 shown in FIG. 1 (a step 1500), an inspecting condition setting window shown in FIG. 16 is displayed on the display 136. Inspecting conditions 501 include elements of a primary optics system such as a wafer name, specimen incident energy of the primary beam, probe current and surface electric field intensity, elements of the detector such as pixel size and a stage move rate. As a condition of the electron optics system varies when an element of the primary optics system is varied and SN ratio in detecting a defect varies when an element of the detector and a stage move rate are varied, parameters corresponding to each condition of the primary optics system are required to be stored in the memory 132. The operator inputs required data in fields of the inspecting conditions 501, inputs a name of the inspecting conditions in a field of a file name 500, determines the inspecting conditions, and presses a setting button 1603 (a step 1501).

Hereby, various parameters 502 which are conditions corresponding to the inspecting conditions 501 of the electron optics system are determined. In the parameters 502, G denotes voltage applied to the electron gun 101, L denotes the excitation current of the lens in the optics system, AL denotes various aligners, ST denotes a stigmator, V denotes various voltage, S denotes voltage applied to an electrostatic lens, and a numeral following each letter denotes the number of each element. However, all these elements are not shown in FIG. 1. When the parameters 502 are determined, the system controller 135 determines voltage applied to the electron gun 101, respective output current and respective output voltage to an extractor electrode (not shown) inside the electron gun, the power supply for retarding voltage 118*a*, the power supply for surface-electric-field controlling voltage 118*b*, the electromagnetic lens 104 that superposes a magnetic field in the electron gun, the collimator lens 107, the lens array 109, the objective lens 112, the beam separator 111, the deflector for scanning 113 and various aligners (not shown). When inspecting conditions are determined, calibration is executed in parallel for all beams, namely, multi-beams (a step 1502). The setting of the inspecting conditions is also finished by the completion of the calibration (a step 1503). In this embodiment, the setting of inspecting conditions and the calibration are continuously executed, however, only inspecting conditions are predetermined and calibration may be also executed later.

Figure 4:
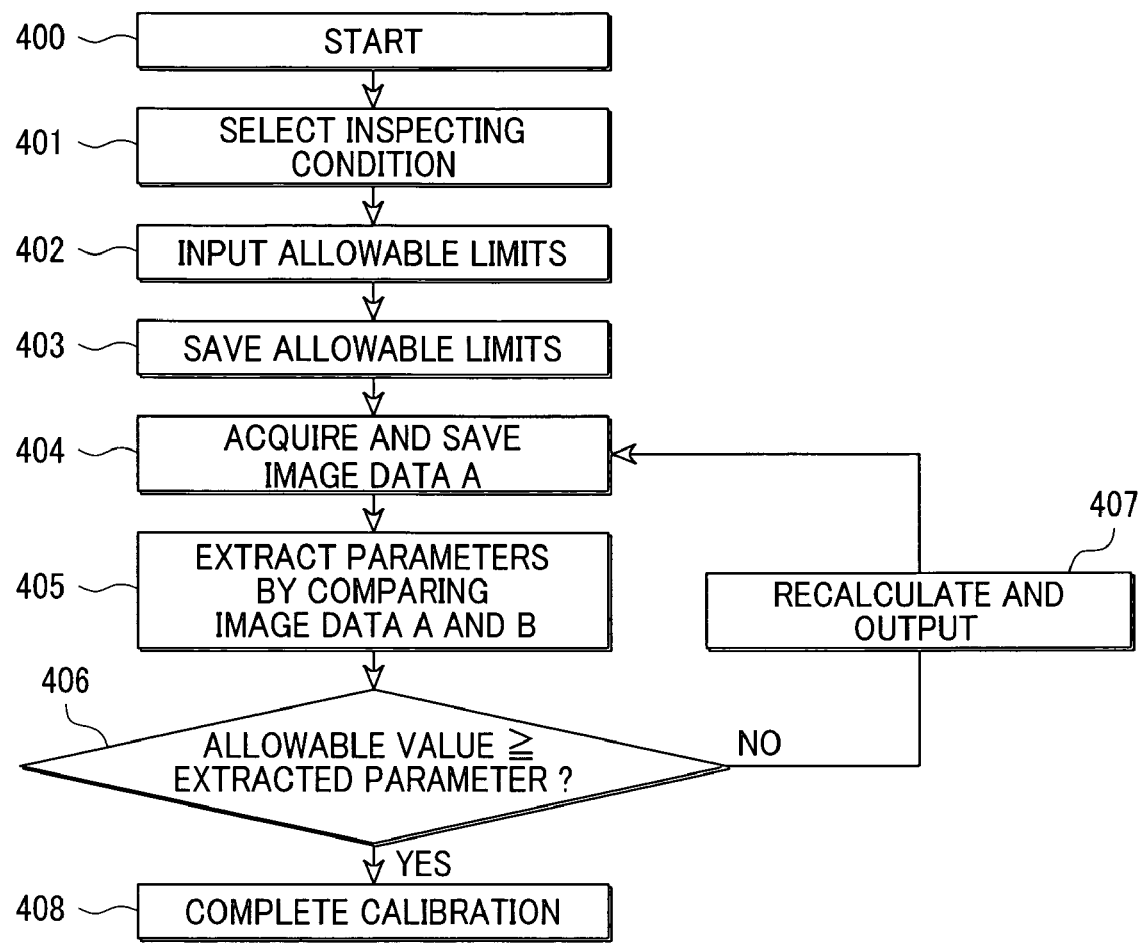
FIG. 4 is a flowchart showing a procedure for the calibration of primary beams in the first embodiment.

FIG. 4 is a flowchart showing a procedure for the calibration of primary beams. When the operator clicks a calibration button displayed on the display 136 shown in FIG. 1 (a step 400), the stage 117 is moved so that the reference mark 116 is located in a field of view. While calibration is executed, the stage 117 is not moved, and a still image is acquired with a deflection direction in two directions of a deflection direction under inspection and its perpendicular direction. When the move of the stage 117 is finished, an inspecting condition selecting window shown in FIG. 5 is displayed on the display 136. The configuration of the inspecting condition selecting window is basically similar to the inspecting condition setting window shown in FIG. 16 and the inspecting condition selecting window includes an inspecting condition file name 500, inspecting conditions 501, various parameters 502 and an importation button 503. When the operator inputs or selects an inspecting condition file name 500 and reads an inspecting condition file, the system controller 135 determines voltage applied to the electron gun 101, respective output current and respective output voltage to the extractor electrode (not shown) inside the electron gun, the power supply for retarding voltage 118*a*, the power supply for surface-electric-field controlling voltage 118*b*, the electromagnetic lens 104 that superposes a magnetic field in the electron gun, the collimator lens 107, the lens array 109, the objective lens 112, the beam separator 111, the deflector for scanning 113 and various aligners (not shown).

Figure 6:
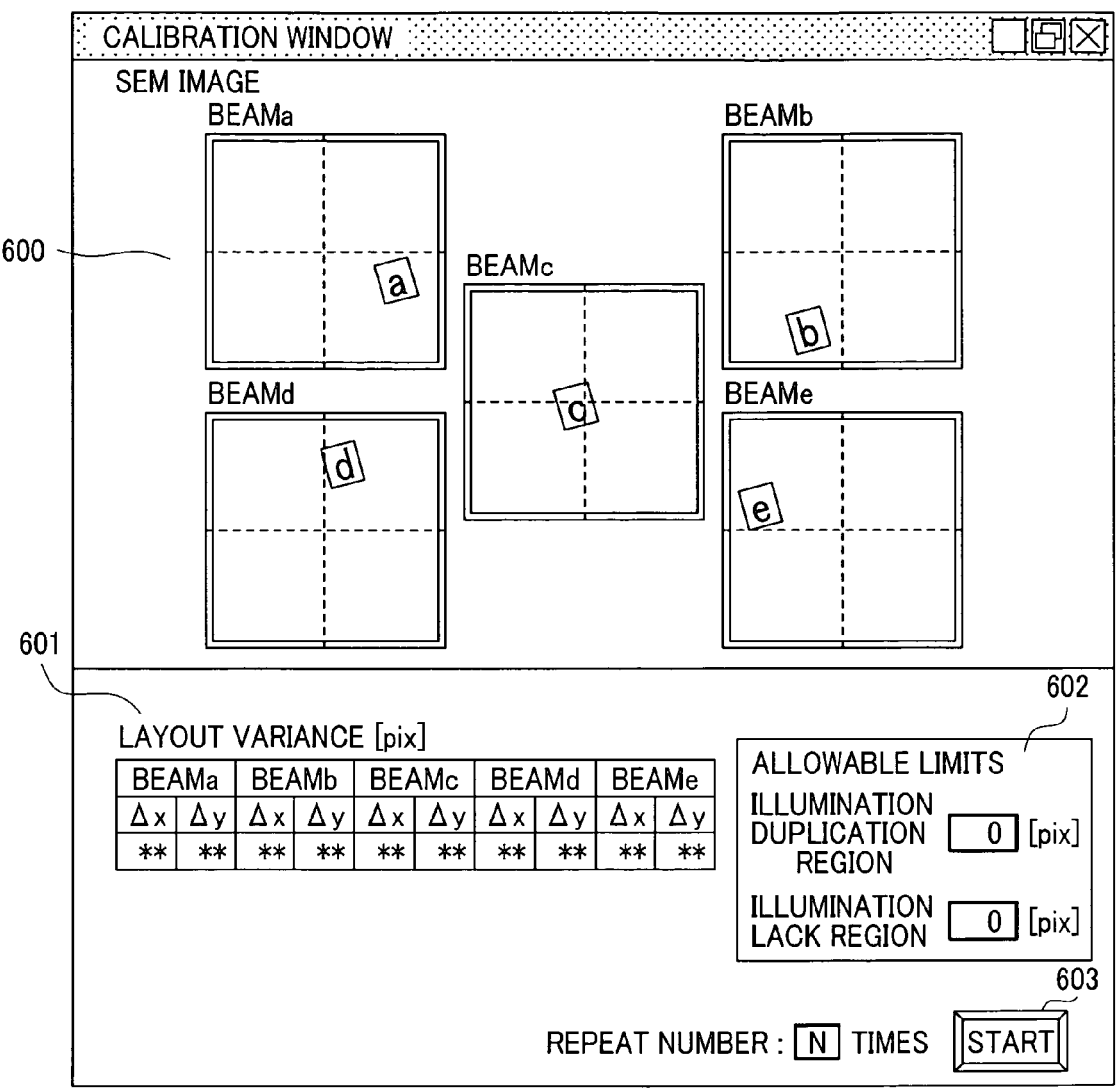
FIG. 6 shows a calibration window for primary beams in the first embodiment.

When the operator clicks the importation button 503 and determines inspecting conditions (a step 401), a calibration window shown in FIG. 6 is displayed on the display 136. The calibration window mainly includes acquired images 600 including each reference mark 300*a* to 300*e* shown in FIGS. 3A to 3C by each primary beam and a parameters displayed part 601. The operator inputs respective allowable pixel numbers of missing pixels and overlapped pixels in a tolerance input box 602 based upon the displayed information (a step 402). When the operator clicks a start button 603 shown in FIG. 6, numeric values (hereinafter called allowable numeric values) input in the tolerance input box 602 are stored in the memory 132 (a step 403). All the primary beams as multi-beams irradiate the vicinity of each reference mark 300*a* to 300*e*, the detectors 121*a* to 121*c* detect generated each secondary beam, the amplifiers 130*a* to 130*c* amplify each secondary beam, the A/D converter 131 digitizes each secondary beam, and each data is stored in the memory 132 as the image data (hereinafter called image data A) of each reference mark 300*a* to 300*e* (a step 404). Simultaneously at this time, each data is displayed on the display 136 as acquired images 600.

In the memory 132, images (hereinafter called image data B) acquired when a layout of the primary beams is ideal of the reference marks 300*a* to 300*e* are stored beforehand. Then, the computer 133 simultaneously extracts parameters required for the calibration of the primary beams for all images by comparing the image data A with the image data B (a step 405).

The computer 133 feedbacks conditions related to all the primary beams as multi-beams of the electron optics system in parallel until the computer compares the extracted parameters and allowable numeric values stored in the memory 132 and judges the variance of all the primary beams as multi-beams to be within tolerance (a step 406). The feedback is executed by recalculating values output to the scanning signal generator 137 and the electron optics system controller 139 by comparing the extracted parameters and the allowable numeric values stored in the memory 132 and outputting the values again (a step 407). This is repeated and when the computer 133 judges image variance by all the beams as multi-beams to be within the tolerance as a result of comparing the image data A and the image data B or when the operator judges the image variance to be within the tolerance, the calibration of the primary beams is completed (a step 408). For the judgment 406 of whether the calibration of the primary beams is completed or not, the operator manually repeats the calibration, may also judge it by himself/herself or the operator inputs a repetitive frequency beforehand, and the control system may be also configured so that the calibration is completed when a desired condition is acquired in the repetitive frequency, an error is displayed when a desired condition is not acquired and the calibration is finished.

Second Embodiment

Figure 7:
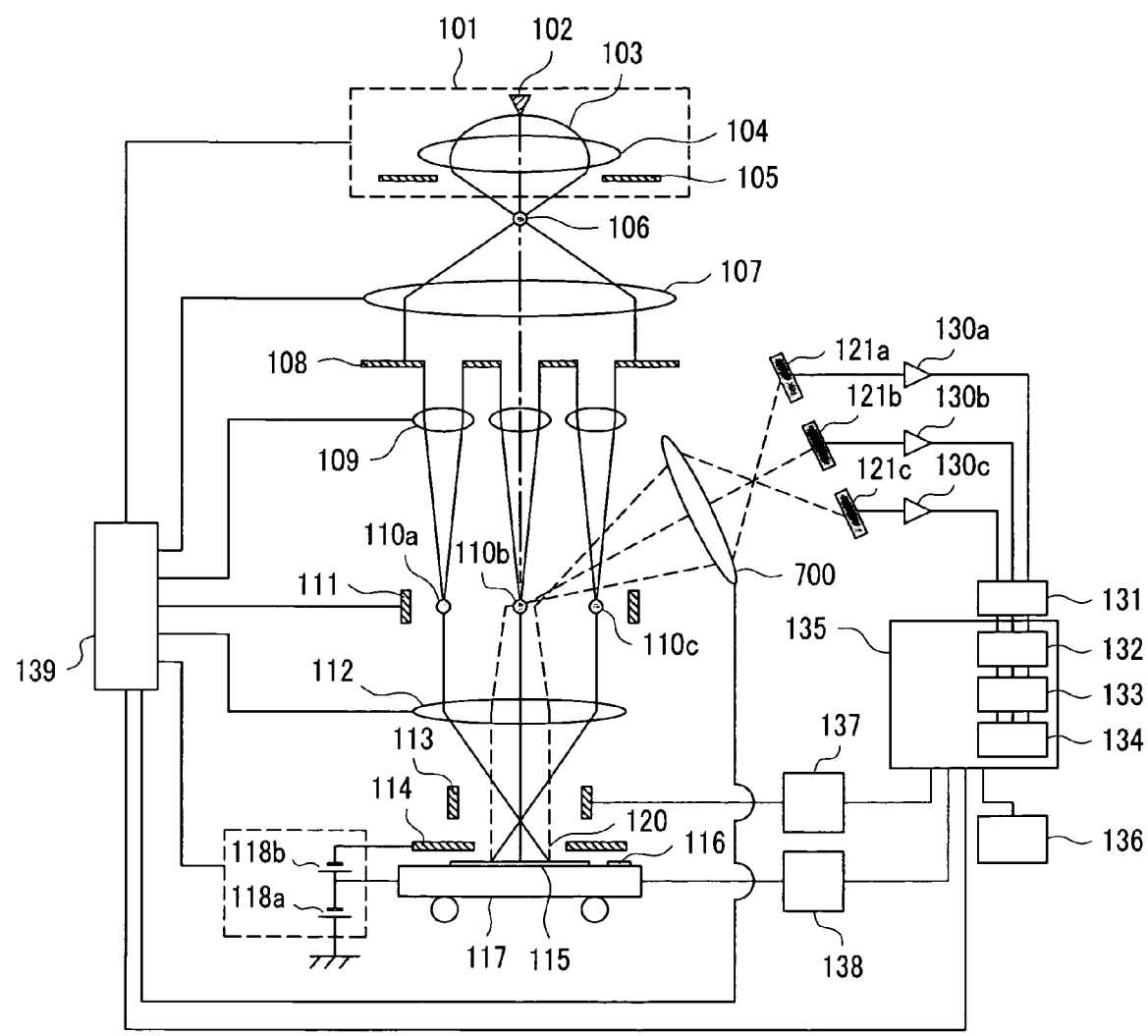
FIG. 7 illustrates the configuration of a multi-electron-beam inspection system equivalent to a second embodiment.

FIG. 7 shows the schematic configuration of an electron beam inspection system equivalent to a second embodiment.

When the configuration of the system in this embodiment is compared with that in the first embodiment, an electromagnetic lens 700 is added to a secondary optics system and an image of secondary electrons generated from a wafer 115 which is a specimen is extended and projected on secondary electron detectors 121a to 121c. A secondary beam 120 is rotated or is extended (is reduced) by the effect of an objective lens 112 and the electromagnetic lens 700 and the quantity of the rotation and the extension varies every inspecting condition like a layout when a primary beam reaches a surface of the wafer 115. Then, in this embodiment, the calibration of plural secondary beams is executed at the same time with the calibration of the primary beams.

Figure 8A:
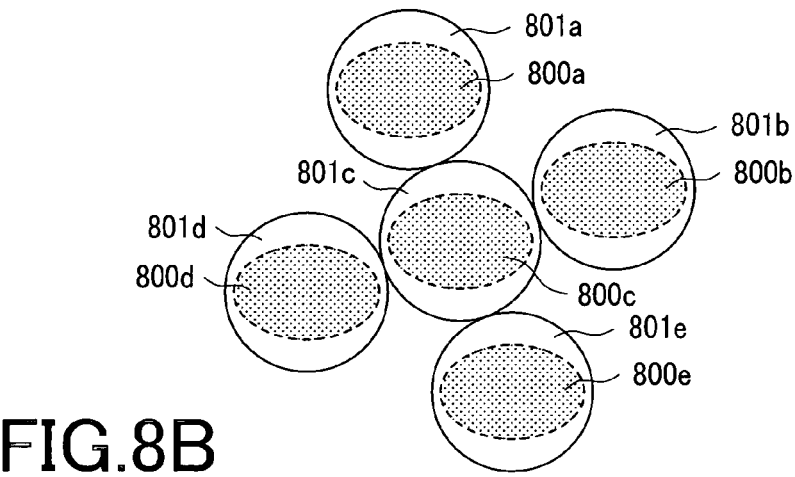
FIGS. 8A to 8C are schematic plans showing secondary electron detectors in the second embodiment.
Figure 8B:
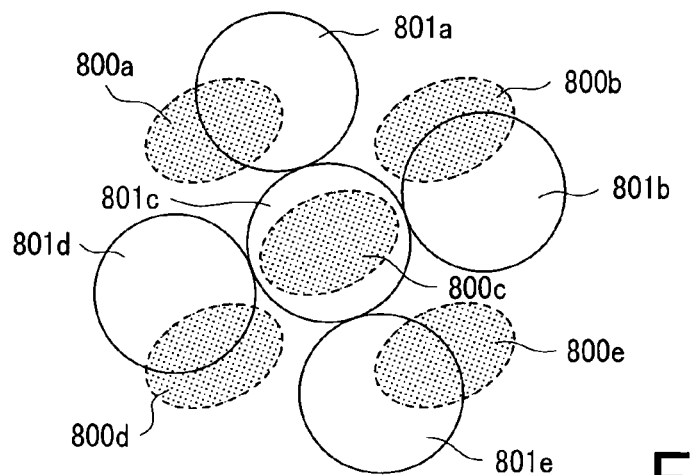
Figure 8C:
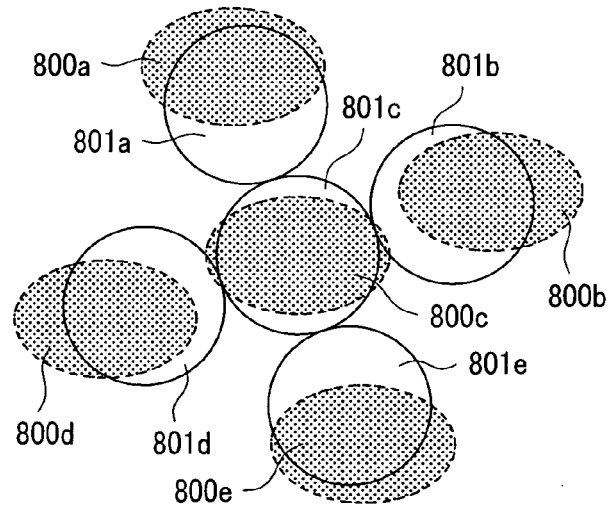

FIGS. 8A to 8C are schematic plans showing secondary electron detector positions. When the rotation of plural secondary beams is ideal, secondary beam detector reached positions 800a to 800e coincide with positions 801a to 801e of the secondary electron detectors as shown in FIG. 8A. However, when the plural secondary beams is rotated by the effect of the objective lens 112 and the electromagnetic lens 700, secondary beam detector reached positions are variant with the positions 801a to 801e of the secondary electron detectors as shown in FIG. 8B. When a magnification is ill-fitted, secondary beam detector reached positions 800a to 800e are protruded without being settled in the positions 801a to 801e of the secondary electron detectors as shown in FIG. 8C. Therefore, secondary electron current detected by the secondary electron detectors 121a to 121c decreases, compared with an ideal state, and a problem that the brightness of an acquired image is insufficient occurs.

As the quantity of current incident on the secondary electron detector is maximum when the secondary beam detector reached positions 800a to 800e coincide with the positions 801a to 801e of the secondary electron detectors, secondary beam calibration can be executed by measuring current in the detector and feed backing the electromagnetic lens 700 to search a position in which the quantity of current is maximum.

Even if the calibration of each of a plural secondary beams is executed and current flowing in each secondary electron detector 121a to 121c is maximum, difference may be made in the brightness of an acquired image because of an effect of optical aberration and others upon the secondary optics system. Then, in this embodiment, when difference is made in current acquired by each secondary electron detector 121a to 121c, the gain of the detector is varied and undercurrent is compensated.

Next, a procedure for executing the above-mentioned secondary beam calibration will be described. The secondary beam calibration has only to be executed without a break after primary beam calibration.

Figure 9:
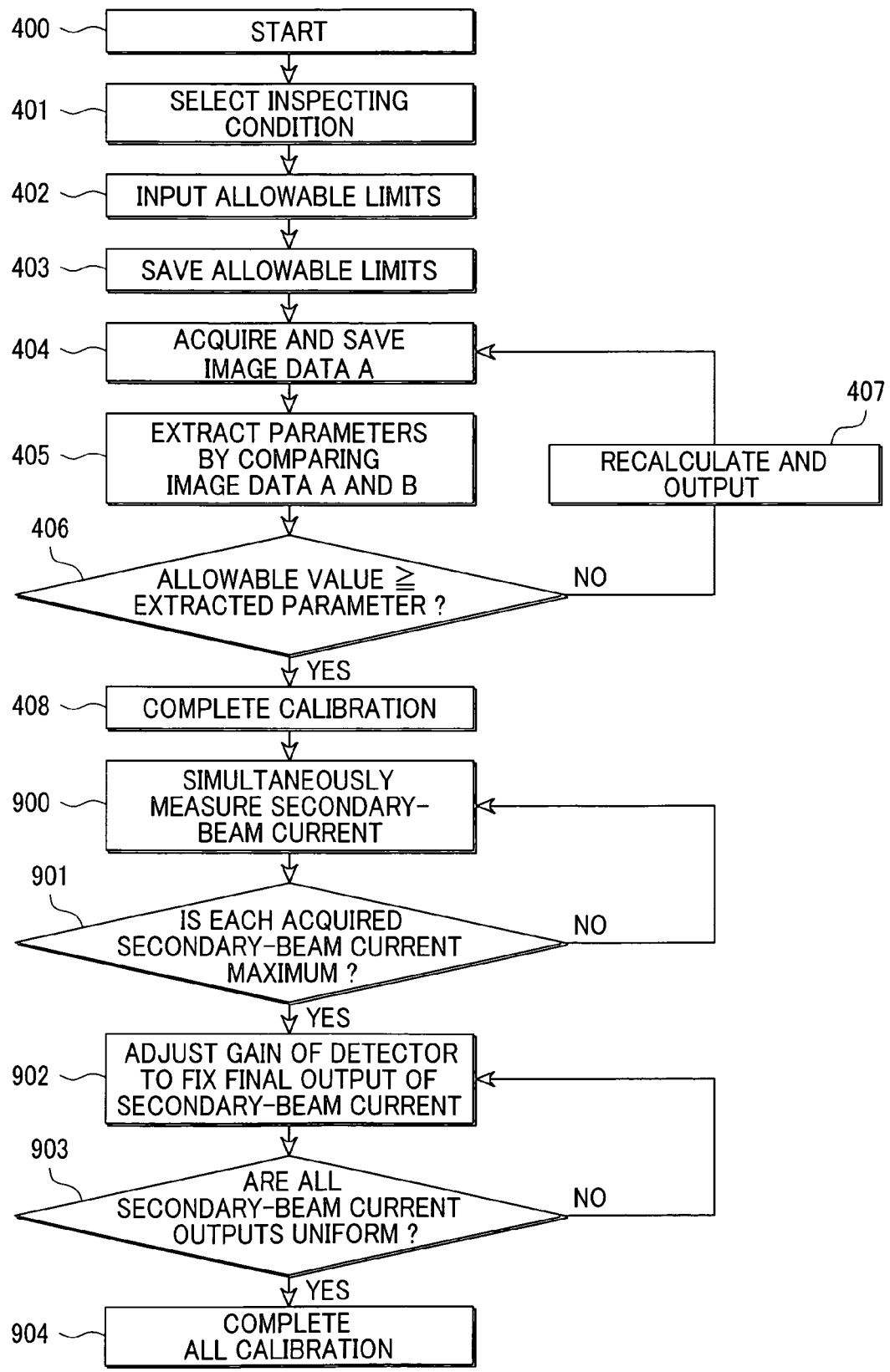
FIG. 9 is a flowchart showing a procedure for calibration in the second embodiment.
Figure 10:
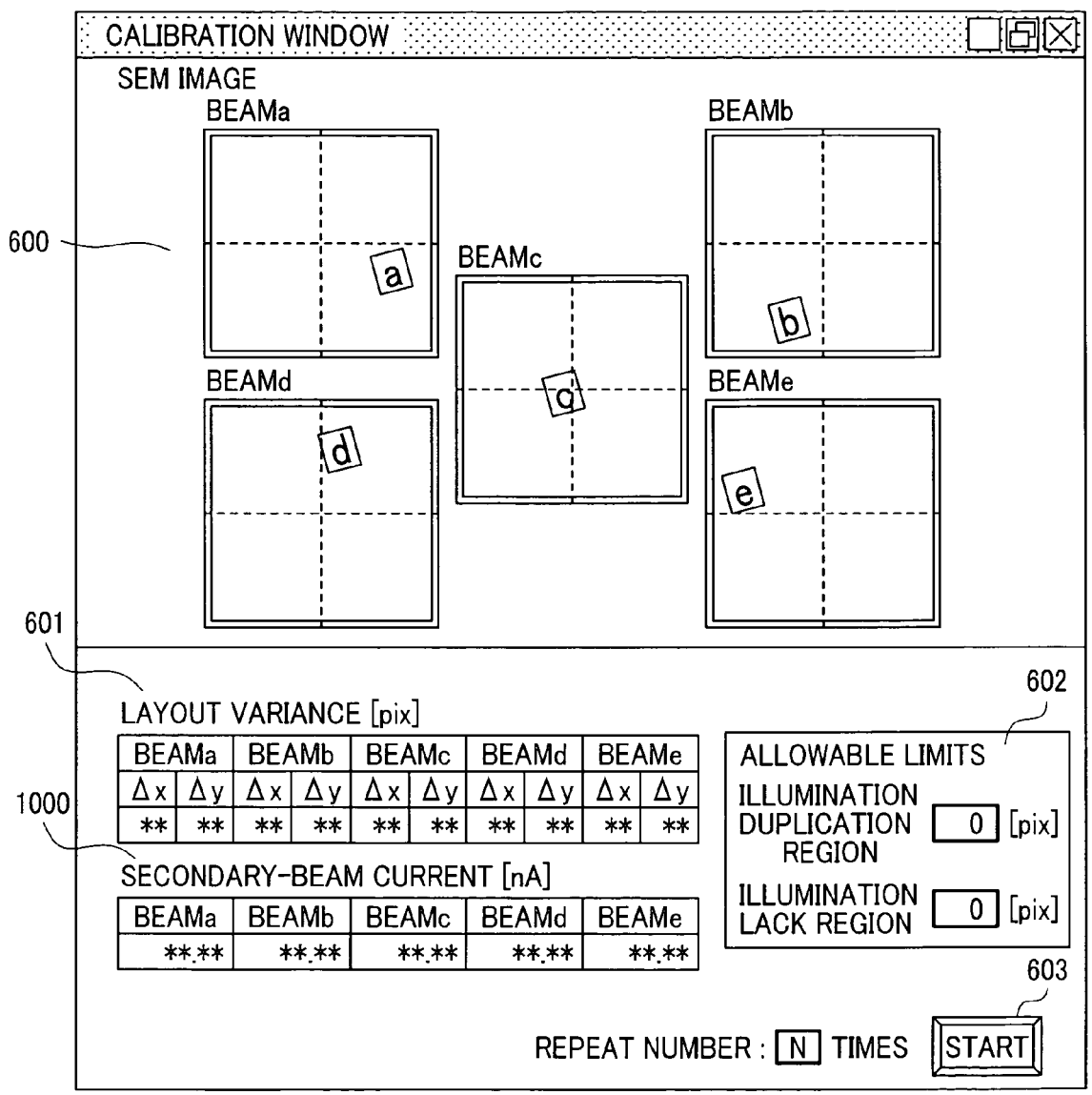
FIG. 10 shows a calibration window in the second embodiment.

FIG. 9 is a flowchart showing the procedure for secondary beam calibration. When an operator clicks a calibration button displayed on a display 136 shown in FIG. 1 (a step 400), a stage 117 is moved so that a reference mark 116 is located in a field of view. When the move of the stage 117 is finished, an inspecting condition selecting window shown in FIG. 5 is displayed on the display 136. It is also described in the first embodiment that a condition of an electron optics system greatly changes every inspecting condition 501. The operator inputs an inspecting condition file name 500 stored in a memory 132 on the window shown in FIG. 5 or selects it and reads data. Hereby, a system controller 135 determines various output current and various output voltage. When the operator clicks a determination button and determines inspecting conditions (a step 401), a calibration window shown in FIG. 10 is displayed on the display 136. The calibration window mainly includes acquired images 600 including reference marks 300a to 300e shown in FIGS. 3A to 3C by each primary beam and a parameter display part 601. When FIG. 10 is compared with FIG. 6, a secondary beam current display part 1000 is added to the parameter display part 601. The operator inputs each allowable pixel number of a missing pixel and overlapped pixels in a tolerance input box 602 based upon the display information (a step 402). When the operator clicks a start button 603 in FIG. 6, numeric values (hereinafter called allowable numeric values) input in the tolerance input box 602 are stored in the memory 132 (a step 403). All primary beams, namely, multi-beams irradiate each vicinity of the reference marks 300a to 300e, generated each secondary beam is detected by each detector 121a to 121c, is amplified by each amplifier 130a to 130c, is digitized by an A/D converter 131, and is stored in the memory 132 as image data (hereinafter called image data A) of the reference marks 300a to 300e. Simultaneously at this time, the generated each secondary beam is displayed on the display 136 as each acquired image 600 (a step 404). While calibration is executed, the stage 117 is not moved and a still image is acquired with a deflection direction in two directions of a deflection direction under inspection and its perpendicular direction.

Images (hereinafter called image data B) acquired when a layout of the primary beams is ideal of the reference marks 300a to 300e are stored in the memory 132 beforehand. Then, a computer 133 simultaneously extracts parameters required for the calibration of the primary beams for all images by comparing the image data A with the image data B (a step 405).

The computer 133 compares the extracted parameters and allowable numeric value stored in the memory 132 and feedbacks optical conditions in parallel for all the primary beams as multi-beams until the computer judges that variance is within tolerance for all the beams as multi-beams (a step 406). The feedback is executed by calculating and outputting values output to a scanning signal generator 137 and an electron optics system controller 139 by comparison between the extracted parameters and the allowable numeric values stored in the memory 132. This is repeated and when the computer 133 judges that variance is within tolerance for all the beams as multi-beams as a result of comparing the image data A and the image data B or when the operator judges that variance is within tolerance, the calibration of the primary beams is completed (a step 408).

When primary-beam calibration is finished, secondary-beam calibration is immediately started. Secondary electron current acquired by each secondary electron detector is simultaneously measured (a step 900) and is stored in the memory 132. This is repeated, feed backing from the system controller 135 to the electron optics system controller 139, the computer 133 compares the stored quantity of current, and searches a spot at which respective current is maximum (a step 901). When the computer finds the spot, the computer 133 compares secondary electron current imported by each secondary electron detector and adjusts the gain of each detector so that final output is fixed (a step 902). The computer 133 repeats the adjustment until the final output is uniform as a result of comparing output values (a step 903) and when the computer judges that the final output is uniform or when the operator judges so, all the calibration is finished. As for the judgment 903 that the calibration is completed, the operator inputs a repetitive frequency beforehand and the controllers may be also configured so that the calibration is completed if desired conditions are acquired in the repetitive frequency, an error message is displayed and the calibration is finished if desired conditions are not acquired, or as the operator himself/herself can see images by each beam as the acquired images 600 at this time, the operator manually repeats calibration and may also judge by himself/herself. When initial variance of the primary beams and the secondary beams is great, control is returned to primary-beam calibration again after secondary-beam calibration is finished and higher-precision feedback may be also executed.

In the first and second embodiments, the examples that the calibration of the primary beams is executed depending upon the variation of the conditions of the electron optics system are described. In the following third and fourth embodiment, examples that calibration is executed by the variation of mechanical conditions in addition to the variation of conditions of an electron optics system will be described. The following embodiments will be based upon the schematic block diagram (FIG. 1) showing the electron beam inspection system used in the first embodiment to simplify description, however, the effect will be not lost even if the following embodiments are based upon the second embodiment.

Third Embodiment

Figure 11:
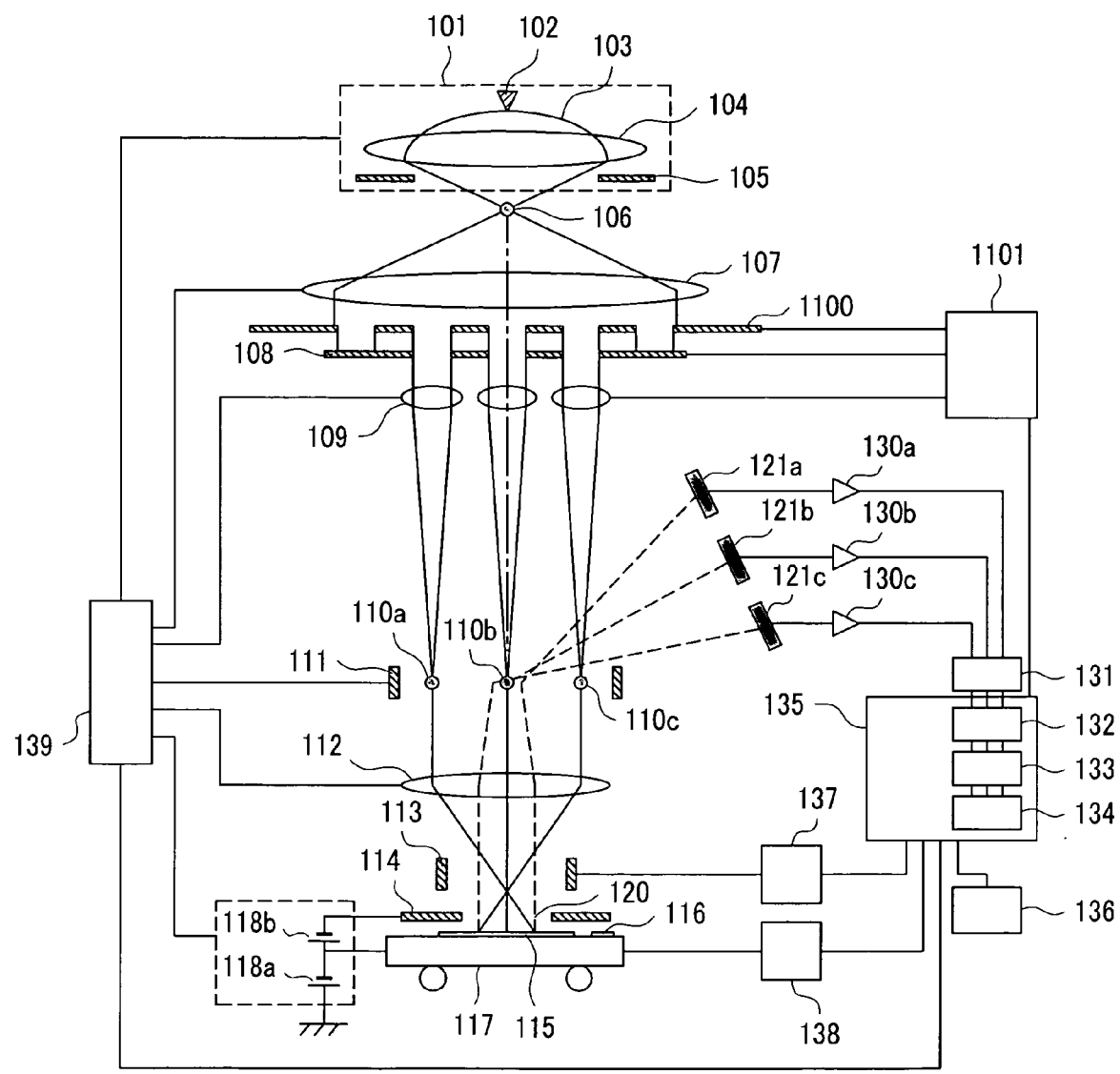
FIG. 11 illustrates the configuration of a multi-electron-beam inspection system equivalent to a third embodiment.

FIG. 11 shows the schematic configuration of an electron beam inspection system equivalent to a third embodiment.

Figure 12A:
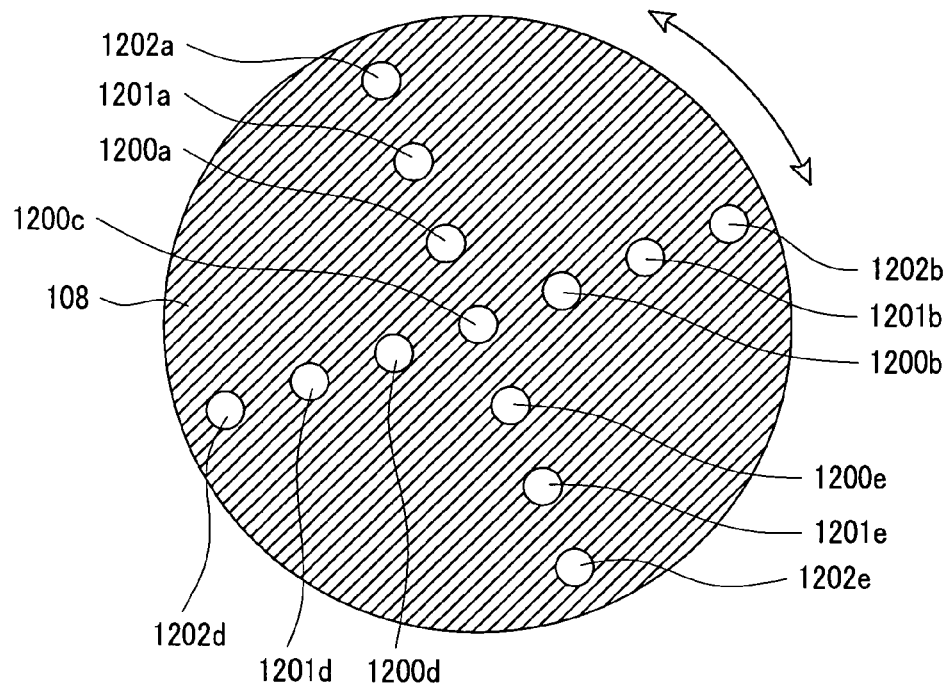
FIGS. 12A and 12B are schematic plans showing aperture arrays 108 and 1100 in the third embodiment.
Figure 12B:
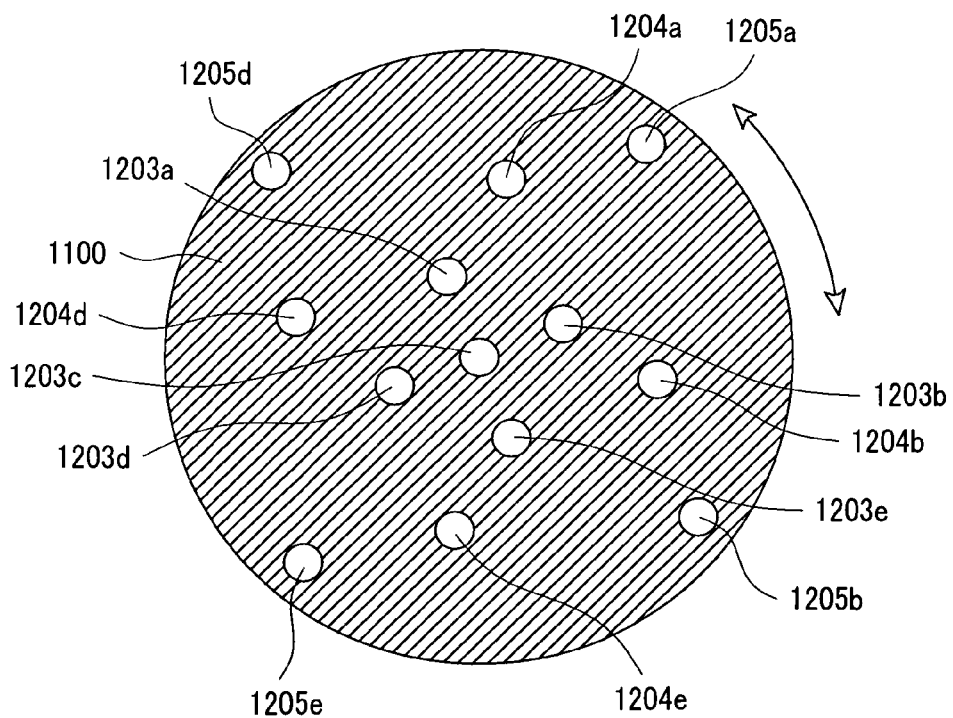

When the configuration of the system in this embodiment is compared with that in the first embodiment, an aperture array 1100 and a mechanical operation control unit 1101 are added. Aperture arrays 108 and 1100 which are charged particle beam selecting devices and a lens array 109 are connected to the mechanical operation control unit 1101 and can be mechanically rotated by the control of a system controller 135. FIGS. 12A and 12B are schematic plans showing each aperture array 108, 1100. An aperture of the lens array 109 is similar to the aperture array 108 though the aperture is not shown in FIGS. 12A and 12B and the lens array 109 is rotated according to the rotation of the aperture array 108. At least two apertures are respectively formed in the aperture arrays 108, 1100.

In FIGS. 12A and 12B, (1) a group of apertures 1200a to 1200e in FIG. 12A and a group of apertures 1203a to 1203e in FIG. 12B, (2) a group of apertures 1201a, 1201b, 1201d, 1201e in FIG. 12A and a group of apertures 1204a, 1204b, 1204d, 1204e in FIG. 12B and (3) a group of apertures 1202a, 1202b, 1202d, 1202e in FIG. 12A and a group of apertures 1205a, 1205b, 1205d, 1205e in FIG. 12B correspond in a one-to-one state in respective layouts of the apertures. They are arranged so that positions of the other groups of apertures do not coincide when the aperture array 108 or 1100 is rotated so that coordinates of certain one group of apertures of (1) to (3) coincide. However, in this embodiment, the number of multi-beams is set to five, and the apertures 1200c and 1203c on a central axis (an optical axis) coincide in any case of the above-mentioned (1) to (3). The above-mentioned (1) to (3) are different in an interval between primary beams. Rotation can be selected by further rotating the following both and varying angles of the apertures in a state in which the aperture arrays 108 and 1100 are relatively rotated so that the apertures of any of the above-mentioned (1) to (3) coincide. Therefore, a layout of primary beams on a surface of a wafer 115 can be adjusted and a calibration function by mechanical adjustment can be added to the calibration by only the adjustment of the electron optics system described in the first and second embodiments.

Fourth Embodiment

Figure 13:
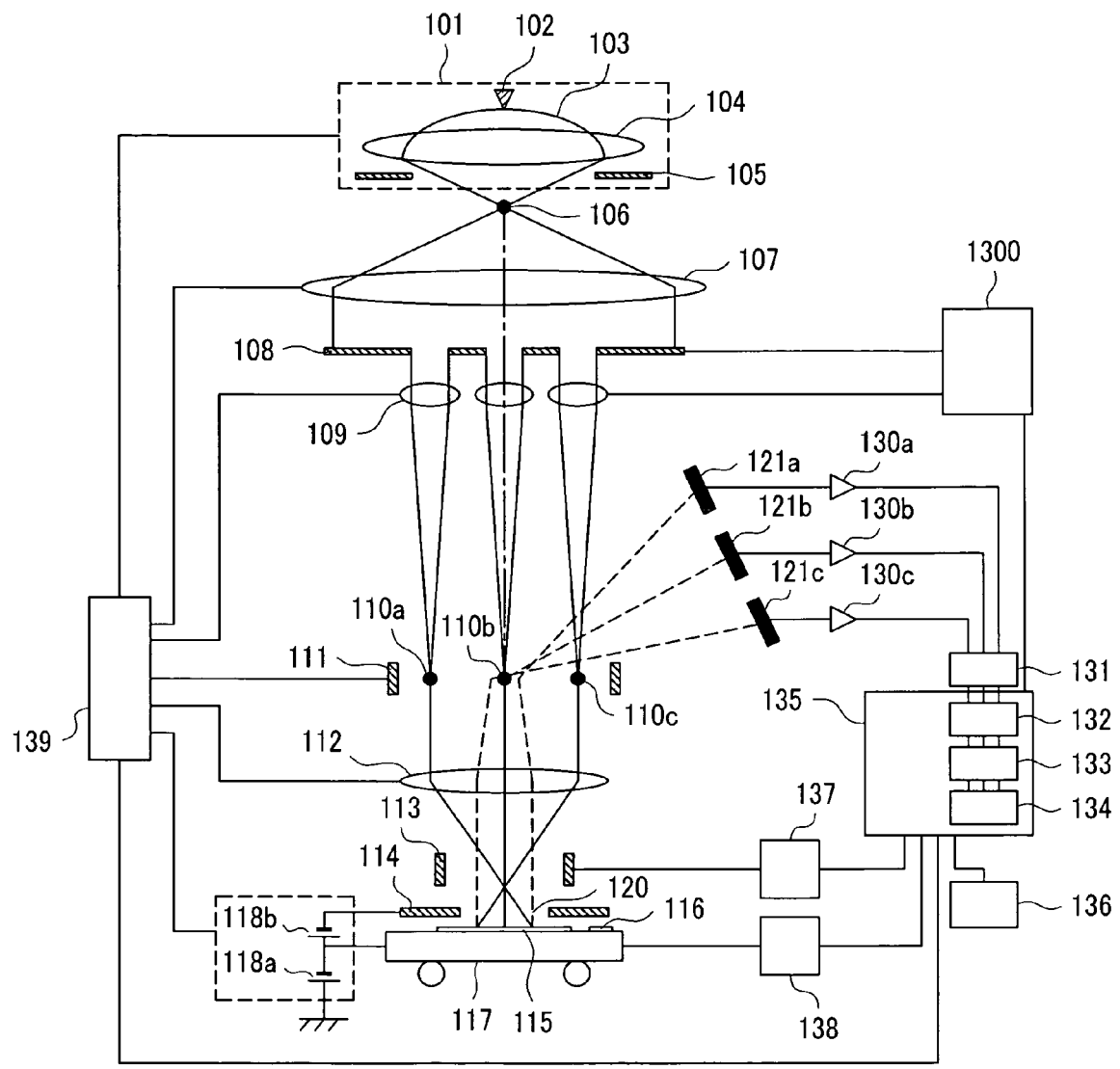
FIG. 13 illustrates the configuration of a multi-electron-beam inspection system equivalent to a fourth embodiment.

FIG. 13 shows the schematic configuration of an electron beam inspection system equivalent to a fourth embodiment.

Figure 14:
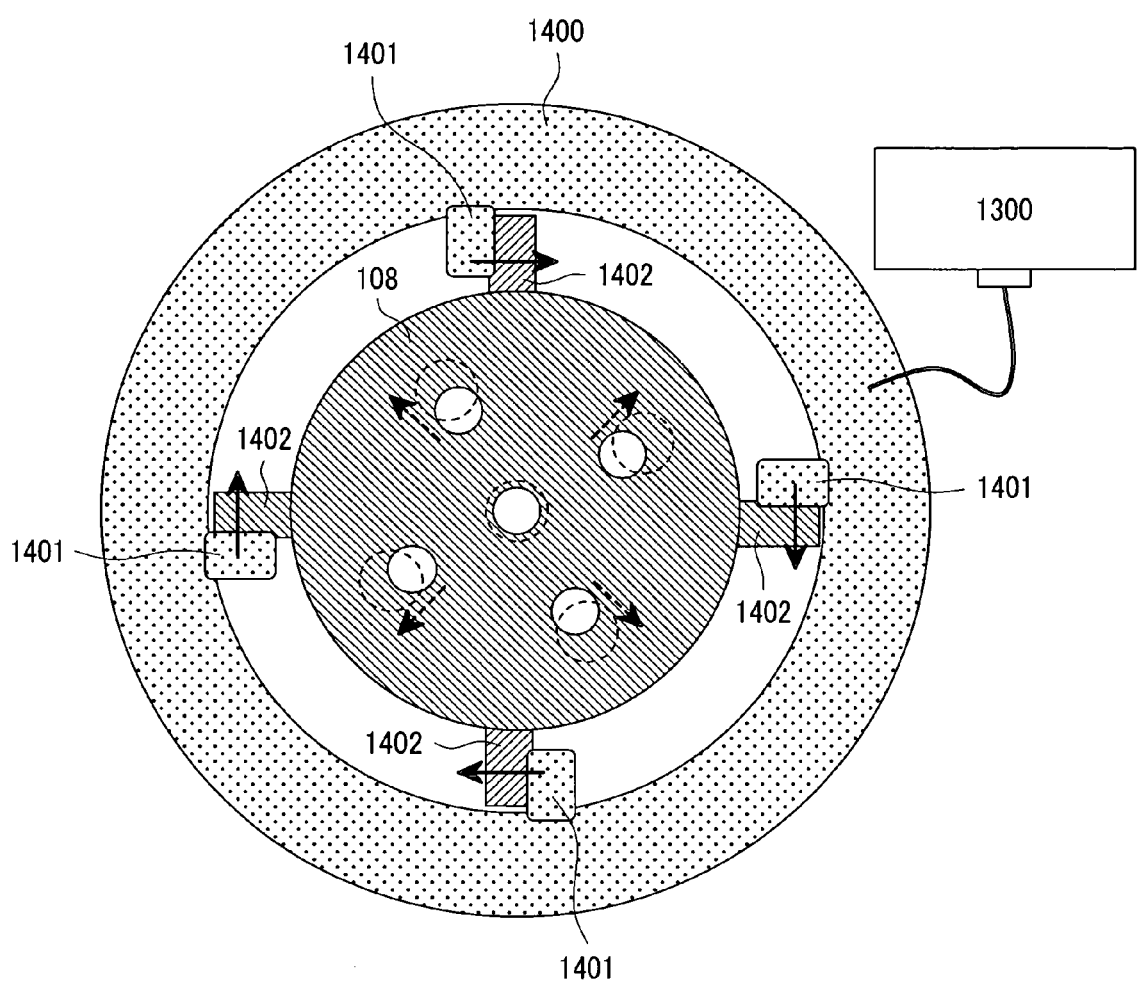
FIG. 14 is a schematic plan showing an aperture array 108 in the fourth embodiment.

When the configuration of the system in this embodiment is compared with that in the first embodiment, a temperature control unit 1300 is added. An aperture array 108 and a lens array 109 are connected to the temperature control unit 1300 and respective temperature can be controlled by a system controller 135. FIG. 14 is a schematic plan showing the aperture array 108 in this embodiment. As shown in FIG. 14, an outer ring 1400 made of material having a thermal expansion coefficient different from the aperture array 108 is installed outside the aperture array 108. The aperture array 108 and the outer ring 1400 are touched in a projection 1402 and a projection 1401 and the temperature control unit 1300 is connected to the outer ring to enable temperature control. When the temperature control unit 1300 is set to high temperature, the aperture array 108 expands in directions shown by dotted arrows because of thermal expansion and a beam interval varies. At this time, the outer ring 1400 also expands, however, as its thermal expansion coefficient is different from that of the aperture array 108, difference is made between the projections 1402 and 1401 in an expansion coefficient and as a result, force is applied in directions shown by arrows shown by a full line. Therefore, rotation and the variation of an interval between primary beams are enabled by the control of temperature and a calibration function by temperature control can be added to the calibration by only the adjustment of the electron optics system described in the first and second embodiments. Though the lens array 109 is not shown in FIG. 14, the lens array 109 also has the similar configuration to that of the aperture array 108 and expands by heat like the aperture array 108.

In the above-mentioned each embodiment, the examples related to the inspection using electron beams of a semiconductor pattern are described, however, when an ion beam is used or when a magnetic disk is inspected and further, when measurement is made, the effect of the invention is also not lost.

What is claimed is:

1. A charged particle beam apparatus that emits charged particle beams onto a specimen and utilizes generated secondary charged particle beams, comprising:
   a charged particle beam generator that generates a plurality of charged particle beams;
   a primary optics system including at least one lens that makes the plurality of charged particle beams irradiate the specimen and a deflector that deflects the plurality of charged particle beams to scan the specimen;
   signal detectors that individually detect a plurality of secondary charged particle beams generated from a plurality of locations on the specimen by the irradiation of the plurality of charged particle beams;
   a secondary optics system that makes the plurality of secondary charged particle beams incident on the signal detectors;
   a stage onto which the specimen is loaded and which can carry the specimen;
   a display that displays images based upon outputs of the signal detectors; and a first adjuster that adjusts positions on a surface of the specimen which the plurality of charged particle beams irradiate, wherein a layout of a plurality of reference marks, each of which is corresponding to each of the plurality of charged particle beams, are provided on the stage; and the first adjuster adjusts a position on the specimen, which each of the plurality of charged particle beams irradiates, based upon an image of each of the plurality of reference marks on the stage displayed on the display at a standstill during calibration, and measures a layout of the plurality of charged particle beams on the specimen, and carries out calibration of the plurality of charged particle beams at the same time.

2. The charged particle beam apparatus according to claim 1, further comprising:

a memory that stores an operating condition of at least one of the primary optics system, the signal detectors and the stage, determined based upon characteristics of the specimen, wherein the first adjuster adjusts positions on the specimen which the plurality of charged particle beams irradiate, referring to the stored operating condition.

3. The charged particle beam apparatus according to claim 1, wherein the operating condition is a move rate of the stage.

4. The charged particle beam apparatus according to claim 1, wherein the charged particle beam generator that generates the plurality of charged particle beams includes at least two charged particle beam selectors having at least each two apertures for passing each charged particle beam and a mechanical operation control unit that mechanically rotates the charged particle beam selector.

5. The charged particle beam apparatus according to claim 1, wherein the charged particle beam generator that generates the plurality of charged particle beams is provided with at least two charged particle beam selectors for passing each charged particle beam and further, a temperature control unit that is arranged in contact with the charged particle beam selector, configured by a member different in a thermal expansion coefficient from the charged particle beam selector and controls the temperature of the charged particle beam generator.

6. The charged particle beam apparatus according to claim 1, comprising:

a second adjuster for adjusting positions on the signal detectors which the plurality of secondary charged particle beams irradiate.

7. The charged particle beam apparatus according to claim 6, wherein the second adjuster is an electromagnetic lens.

8. The charged particle beam apparatus according to claim 6, further comprising:

a memory that stores an operating condition of at least one of the primary optics system, the signal detectors and the stage, determined based upon characteristics of the specimen, wherein the first adjuster adjusts positions on the specimen which the plurality of charged particle beams irradiate, referring to the stored operating conditions.

9. A charged particle beam apparatus that emits charged particle beams onto a specimen and utilizes generated secondary charged particle beams, comprising:

a charged particle beam generator that generates a plurality of charged particle beams;

a primary optics system including one or more lens that makes the plurality of charged particle beams irradiate the specimen and a deflector that deflects the plurality of charged particle beams to scan the specimen;

signal detectors that individually detect a plurality of secondary charged particle beams generated from a plurality of locations on the specimen by the irradiation of the plurality of charged particle beams;

a secondary optics system that makes the plurality of secondary charged particle beams incident on the signal detectors;

a stage onto which the specimen is loaded and which can carry the specimen;

a display that displays images based upon outputs of the signal detectors; and a second adjuster that adjusts positions on the signal detectors which the plurality of secondary charged particle beams irradiate in order to maximize a secondary electron current detected by each of the signal detectors, wherein each of the signal detectors reaches a position coincides with a position of the signal detector for obtaining the maximum of the secondary electron current.

10. The charged particle beam apparatus according to claim 9, wherein the second adjuster is an electromagnetic lens.

11. A specimen inspection method of emitting charged particle beams onto a specimen on a movable stage and inspecting the specimen utilizing generated secondary charged particle beams, comprising the steps of:

generating a plurality of charged particle beams;

irradiating the stage by the plurality of charged particle beams using a primary optics system;

making a plurality of secondary charged particle beams generated from a plurality of locations on the specimen reach signal detectors using a secondary optics system and individually detecting the plurality of secondary charged particle beams;

displaying acquired images acquired by processing detection signals of the detected plurality of secondary charged particle beams on a display;

measuring respective positions on the stage which the plurality of charged particle beams irradiate using the displayed acquired images;

adjusting the primary optics system based upon the measured irradiated positions;

forming a plurality of reference marks corresponding to each of the plurality of charged particle beams on the stage; and emitting each of the plurality of charged particle beams onto the corresponding plurality of reference marks, measuring a position which each of the plurality of charged particle beams irradiates using the acquired images of the plurality of reference marks and adjusting the primary optics system based upon each of the measured irradiated positions at a standstill during calibration;

measuring a layout of the plurality of charged particle beams on the specimen; and carrying out calibration of each of the plurality of charged particle beams at the same time.

12. The specimen inspection method according to claim 11, comprising the steps of:

determining inspecting conditions of at least one of the primary optics system, the signal detectors and the stage based upon characteristics of the inspected specimen.

13. The specimen inspection method according to claim 12,
wherein the inspecting conditions include a move rate of the stage.

14. The specimen inspection method according to claim 12, comprising the steps of:
storing inspecting conditions determined based upon characteristics of the specimen on at least one of the primary optics system, the signal detectors and the stage; and
adjusting the primary optics system based upon the stored inspecting conditions.

15. The specimen inspection method according to claim 14, comprising the steps of:
measuring positions on the signal detectors which the plurality of secondary charged particle beams irradiate; and
adjusting the positions on the signal detectors which the secondary charged particle beams irradiate based upon the measured results.

16. A charged particle beam apparatus that emits charged particle beams onto a specimen and utilizes generated secondary charged particle beams, comprising:
a charged particle beam generator that generates a plurality of charged particle beams;
a primary optics system including at least one lens that makes the plurality of charged particle beams irradiate the specimen and a deflector that deflects the plurality of charged particle beams to scan the specimen;
signal detectors that individually detect a plurality of secondary charged particle beams generated from a plurality of locations on the specimen by the irradiation of the plurality of charged particle beams;
a secondary optics system that makes the plurality of secondary charged particle beams incident on the signal detectors;
a stage onto which the specimen is loaded and which can carry the specimen; and
a display that displays images based upon outputs of the signal detectors,
wherein when the number of the charged particle beams is set to n and a deflection width deflected by the deflector per charged particle beam is set to S, the specimen can be scanned by the plurality of charged particle beams in a state in which width F of a field-of-view acquired by the plurality of charged particle beams meets a condition of $(2n-1)S F (2n+1)S$.

17. The charged particle beam apparatus according to claim 16,
wherein the condition is $(n-1)S \leq F \leq (n+1)S$.

* * * * *